(12) United States Patent
Phillips

(10) Patent No.: US 8,346,804 B2
(45) Date of Patent: Jan. 1, 2013

(54) SYSTEMS, METHODS, AND APPARATUS FOR COMPUTER-ASSISTED FULL MEDICAL CODE SCHEME TO CODE SCHEME MAPPING

(75) Inventor: John N. Phillips, Seattle, WA (US)

(73) Assignee: General Electric Company, Schenectady, NY (US)

( * ) Notice: Subject to any disclaimer, the term of this patent is extended or adjusted under 35 U.S.C. 154(b) by 78 days.

(21) Appl. No.: 12/938,923

(22) Filed: Nov. 3, 2010

(65) Prior Publication Data
US 2012/0110016 A1 May 3, 2012

(51) Int. Cl.
*G06F 17/30* (2006.01)
(52) U.S. Cl. ............... 707/780; 707/758; 714/48
(58) Field of Classification Search .................. None
See application file for complete search history.

(56) References Cited

U.S. PATENT DOCUMENTS

| | | | | |
|---|---|---|---|---|
| 6,035,057 | A * | 3/2000 | Hoffman | 382/159 |
| 6,246,769 | B1 * | 6/2001 | Kohut | 380/45 |
| 6,691,110 | B2 * | 2/2004 | Yang et al. | 1/1 |
| 7,689,365 | B2 * | 3/2010 | Shams | 702/19 |
| 7,937,342 | B2 * | 5/2011 | George et al. | 706/16 |
| 2001/0001852 | A1 * | 5/2001 | Rovinelli et al. | 703/22 |
| 2006/0174170 | A1 * | 8/2006 | Garland et al. | 714/57 |
| 2009/0055378 | A1 * | 2/2009 | Alecu et al. | 707/5 |
| 2009/0290800 | A1 * | 11/2009 | Lo | 382/197 |
| 2011/0066425 | A1 * | 3/2011 | Hudgins et al. | 704/10 |

OTHER PUBLICATIONS

Barrows et al, "Mapping Clinically Useful Terminology to a Controlled Medical Vocabulary", AMIA, Inc, 1994.*

Lussier et al, "Terminological Mapping for High Throughput Comparative Biology of Phenotypes", 2004.*

Zeng et al, "Mapping Medical Vocabularies to the Unified Medical Language System", AMIA, Inc, 1996.*

Wade et al., "Experiences mapping a legacy interface terminology to SNOMED CT," BMC Medical Informatics and Decision Making, 2008, 8(Suppl 1):S3, Oct. 27, 2008 (6 pages).

Sharma et al., "A Framework for Ontologically-Grounded Probabilistic Matching," Georeference Online Ltd. and Department of Computer Science, University of British Columbia, Oct. 14, 2008 (37 pages).

Lee et al., "Ontology integration: Experience with medical terminologies," Computers in Biology and Medicine 36 (2006) pp. 893-919 (27 pages).

* cited by examiner

*Primary Examiner* — Hung Le
(74) *Attorney, Agent, or Firm* — Hanley, Flight & Zimmerman, LLC

(57) ABSTRACT

An example method for mapping of medical code schemes includes processing a plurality of coded concepts to determine a potential match between a code from a first code scheme in the plurality of coded concepts and a code from a second code scheme in the plurality of coded concepts. The method includes assigning a probability to each potential match of a code from the first code scheme and a code from the second code scheme. The method includes generating an alphanumeric indication of the probability of each potential match between the first code scheme and the second code scheme from the plurality of coded concepts and generating a graphical representation of the plurality of coded concepts. The method includes outputting the alphanumeric indication and the graphical representation to a user and accepting user input to select a match between the first code scheme and the second code scheme.

11 Claims, 16 Drawing Sheets

SYSTEMS, METHODS, AND APPARATUS FOR COMPUTER-ASSISTED FULL MEDICAL CODE SCHEME TO CODE SCHEME MAPPING

FIELD

The present invention generally relates to healthcare terminology mapping. In particular, the present invention relates to systems, methods, and apparatus for matching concepts between a plurality of code schemes to map concepts from one code scheme to another.

BACKGROUND

Medical terminology is voluminous, fragmented, and complex. Multiple standards bodies (e.g., Health Level Seven (HL7), World Health Organization (WHO), etc.) make contributions to categorizing and publishing medical vocabularies (e.g. Systematized Nomenclature of Human and Veterinary Medicine (SNOMED), International Classification of Diseases (ICD), Logical Observation Identifier Names and Codes (LOINC), etc.) across multiple healthcare domains (e.g., medical procedures, problem lists, laboratory, etc.).

Most approaches to managing terminologies rely on mapping rules and use of human intervention of terminology engineers or medical coders to understand differences across source vocabularies, to rationalize the organization of data (via hierarchies and relationships), to identify differences in granularity, and to map between codes and synonyms where there is overlap. This process requires a large amount of manpower to maintain an updated vocabulary and is especially burdensome when implementing new systems in an established healthcare organization with an abundance of systems and proprietary codes and synonyms. Combined with internationalization and a desire to share data across healthcare organizations, the problem quickly becomes unmanageable. For this reason, many healthcare IT providers have created their own proprietary codes, relationships, terms, and picklists which remain unintegrated with other systems and terminologies. Otherwise, the human effort involved can occupy a team of humans for months to find matches between terminologies.

BRIEF SUMMARY

Certain examples provide systems, methods, and apparatus to provide clinical terminology services. Certain examples provide a computer-implemented method for mapping of medical code schemes. The example method includes processing a plurality of coded concepts to determine a potential match between a code from a first code scheme in the plurality of coded concepts and a code from a second code scheme in the plurality of coded concepts. The method also includes assigning a probability to each potential match of a code from the first code scheme and a code from the second code scheme. The method further includes generating an alphanumeric indication of the probability of each potential match between the first code scheme and the second code scheme from the plurality of coded concepts and generating a graphical representation of the plurality of coded concepts. Additionally, the method includes outputting the alphanumeric indication and the graphical representation to a user and accepting user input to select a match between the first code scheme and the second code scheme.

Certain examples provide a system for mapping of medical code schemes. The example system includes a code analyzer to process a plurality of coded concepts to determine a potential match between a code from a first code scheme in the plurality of coded concepts and a code from a second code scheme in the plurality of coded concepts and to assign a probability to each potential match of a code from the first code scheme and a code from the second code scheme. The code analyzer is to generate an alphanumeric indication of the probability of each potential match between the first code scheme and the second code scheme from the plurality of coded concepts and to generate a graphical representation of the plurality of coded concepts. The system also includes a user interface to output the alphanumeric and the graphical representation to a user and to accept user input to select a match between the first code scheme and the second code scheme.

Certain examples provide a tangible computer readable storage medium including executable program instructions which, when executed by a computer processor, cause the computer to implement a medical code scheme bulk matching system. The example system includes a code analyzer to process a plurality of coded concepts to determine a potential match between a code from a first code scheme in the plurality of coded concepts and a code from a second code scheme in the plurality of coded concepts and to assign a probability to each potential match of a code from the first code scheme and a code from the second code scheme. The code analyzer is to generate an alphanumeric indication of the probability of each potential match between the first code scheme and the second code scheme from the plurality of coded concepts and to generate a graphical representation of the plurality of coded concepts. The system also includes a user interface to output the alphanumeric and the graphical representation to a user and to accept user input to select a match between the first code scheme and the second code scheme.

Figure 1:
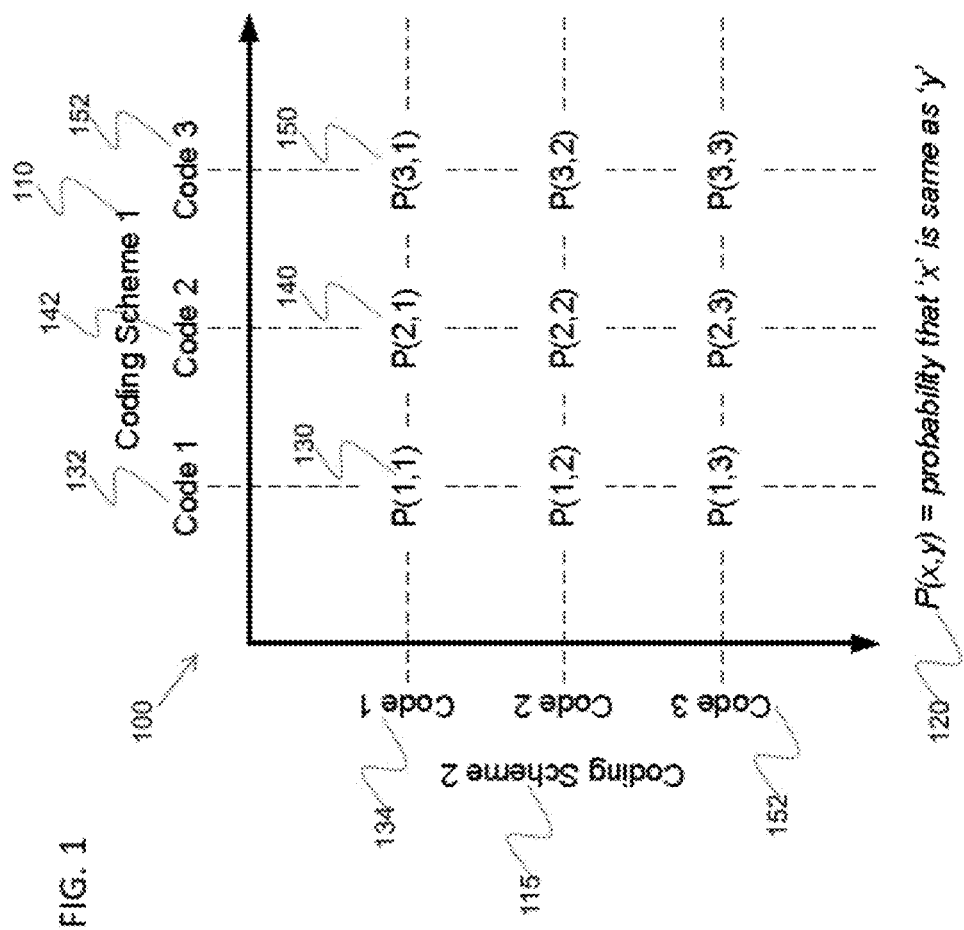
FIG. 1 illustrates an example coding matrix indicating a probability that a code from one scheme matches a code from another scheme.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in an embodiment, at least one of the elements is hereby expressly defined to include a tangible medium such as a memory, DVD, CD, Blu-ray, etc., storing the software and/or firmware.

Certain examples facilitate creation and manipulation of an array of scores wherein each participating code scheme is represented by a dimension and each code in that scheme is a point in that scheme's dimension.

For example, given two different code schemes, each code in scheme 1 represents a row and each code in scheme 2 represents a column. A probability that code 3 in scheme 1 is the same as code 4 in scheme 2 is represented by a cell value at row 3 and column 4 in a code score array. By creating an M×N matrix (where M is a number of codes in scheme 1, and N is a number of codes in scheme 2), a number of visual and mathematical tools can extract meaning. As illustrated in the example coding matrix 100 of FIG. 1, a first coding scheme 110 is compared to a second coding scheme 115 based on a probability P(x,y) 120 that 'x' is the same as 'y'. Thus, the matrix identifies a probability 130 that a first code 132 from the first coding scheme 110 is the same as a first code 134 from the second coding scheme 115, a probability 140 that a second code 142 from the first coding scheme 110 is the same as the first code 134 from the second coding scheme 115, a probability 150 that a third code 152 from the first coding scheme 110 is the same as the first code 134 from the second coding scheme 115, etc. The probability 130, 140, 150 is computed for each possible code combination between the first coding scheme 110 and the second coding scheme 115. An identity matrix:

$$\begin{matrix} 1 & 0 & 0 & 0 \\ 0 & 1 & 0 & 0 \\ 0 & 0 & 1 & 0 \\ 0 & 0 & 0 & 1 \end{matrix}$$

represents an exact A==B mapping, for example.

Figure 14:
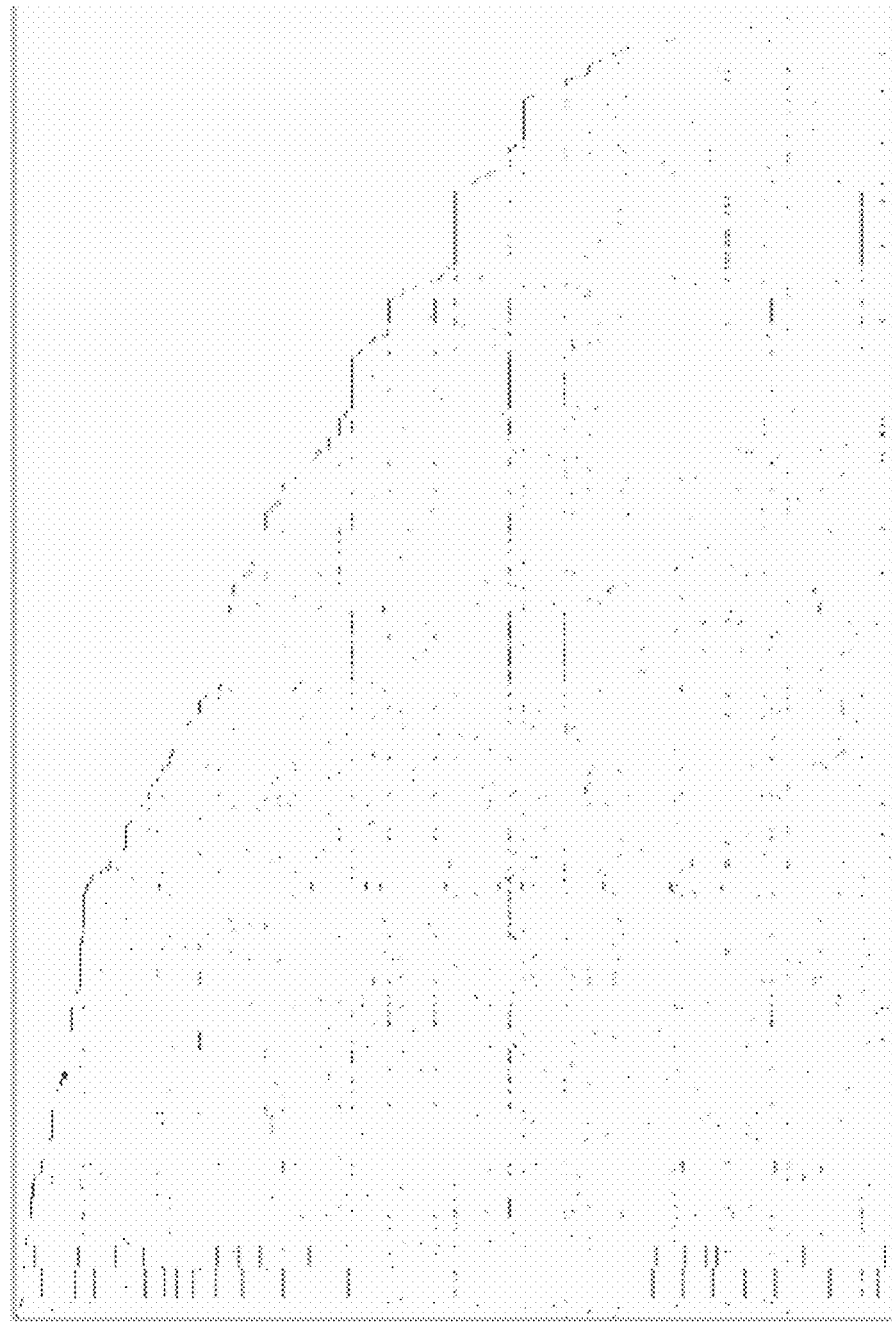
FIG. 14 illustrates an example disbursement of concept matches.

Typically, results of searching for a single concept in a terminology are useable only by a human. A result set is a list of possible matches; some advanced search engines also return a quantitative score. If a goal is to find results for many concepts, then a single-concept-list (SCL) is contributing a single piece to the puzzle. A human must attempt to understand the big picture and manipulate all of the pieces to solve the entire puzzle. As the number of number of concepts to match increases, a number of possible combinations increases exponentially (as illustrated, for example, in FIG. 14). Without an artificial agent, teams of humans can spend many months reducing the set of SCLs into a best-fit solution.

Additionally, an SCL has little or no meaning beyond the scope of its formative search. A human must formalize the SCL into a set of concept-concept mappings that fit a predefined ontology so that an inference engine can draw conclusions.

Clinical information systems typically involve a timetable of three to five years for installation. Even upgrades (of both vendor systems and reference vocabularies) involve many months of expensive content terminology experts.

As demonstrated by the Health Insurance Portability and Accountability Act (HIPAA), even when the government mandates all entities use a single standard (e.g. X12), standards continually evolve and present customers with an ongoing maintenance cost. This problem has received little attention from the research community, probably because they maintain their own terminologies as part of their research. Universities, for example, have the resources to integrate and maintain references and mappings. Research on ontologies and advanced decision support and natural language processing regularly presupposes harmonized terminologies.

A clinical system that is driven by standardized, coded data can help advance analytics, real-time decision support, and business intelligence for healthcare practitioners. In an example, an approach is provided for automating a mapping between external terminologies and use of text-based analysis to provide additional information and presentation of medical codes and terms by supplementing the data with localized clinical content from healthcare providers implementing the clinical system.

To aid a human user in terminology mapping (e.g., confirming a computer-generated match of terms), a graphical indication of what is "known" as well as what is "not known" can be provided. For example, an analyzer can be provided which recognizes both "positive space" (e.g., known or likely matches) and "negative space" (e.g., uncertain matches or crowded sets of terms).

Figure 2:
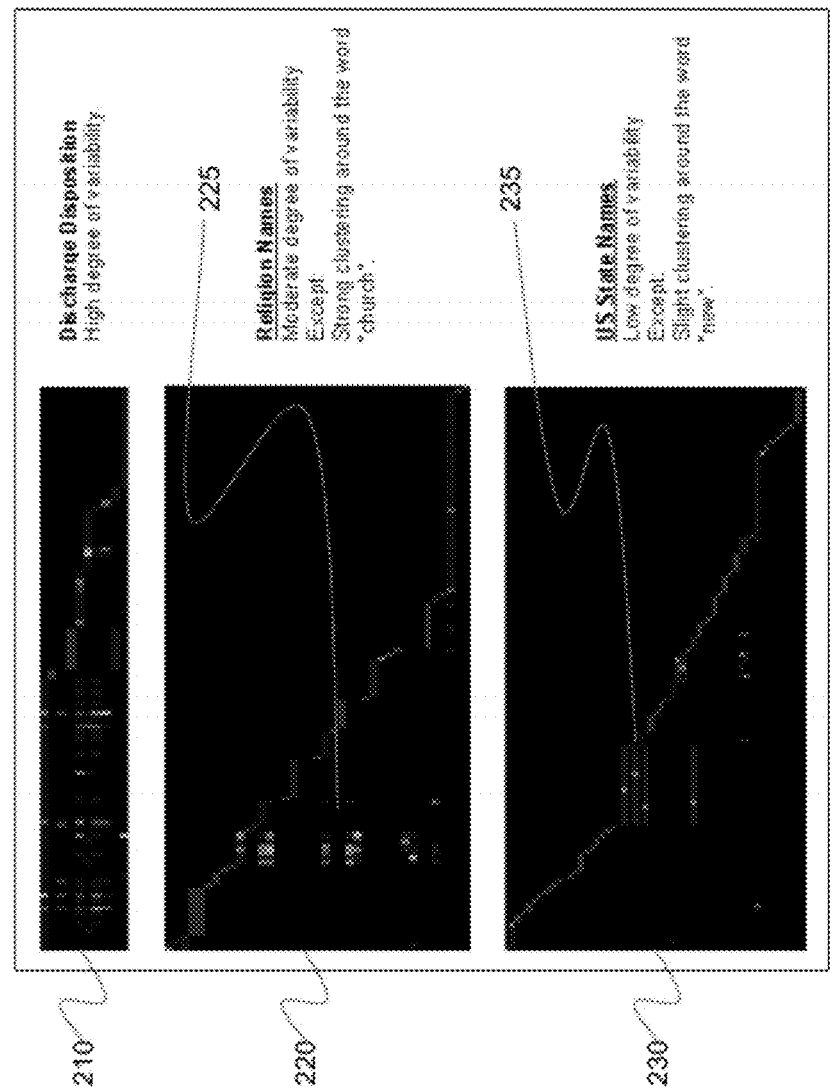
FIG. 2 depicts example graphical visualizations of terms or concepts in a given data set.

In certain examples, clusters of terms/data can be identified. For example, a graphical representation shows the existence of macro-scale concept clustering and visually distinguishes chaotic "tangles" from coherent "one-to-one" mappings. For example, FIG. 2 provides three graphical visualization of terms or concepts in a given data set. As shown in example distribution 210, a high degree of variability exists in the terminology data. Example distribution 220 demonstrates a moderate degree of variability and illustrates strong clustering 225 around a particular term (e.g., "church" in the given example). Example distribution 230 exhibits a low degree of variability and slight clustering 235 around a certain word (e.g., "new" in the given example).

Figure 3:
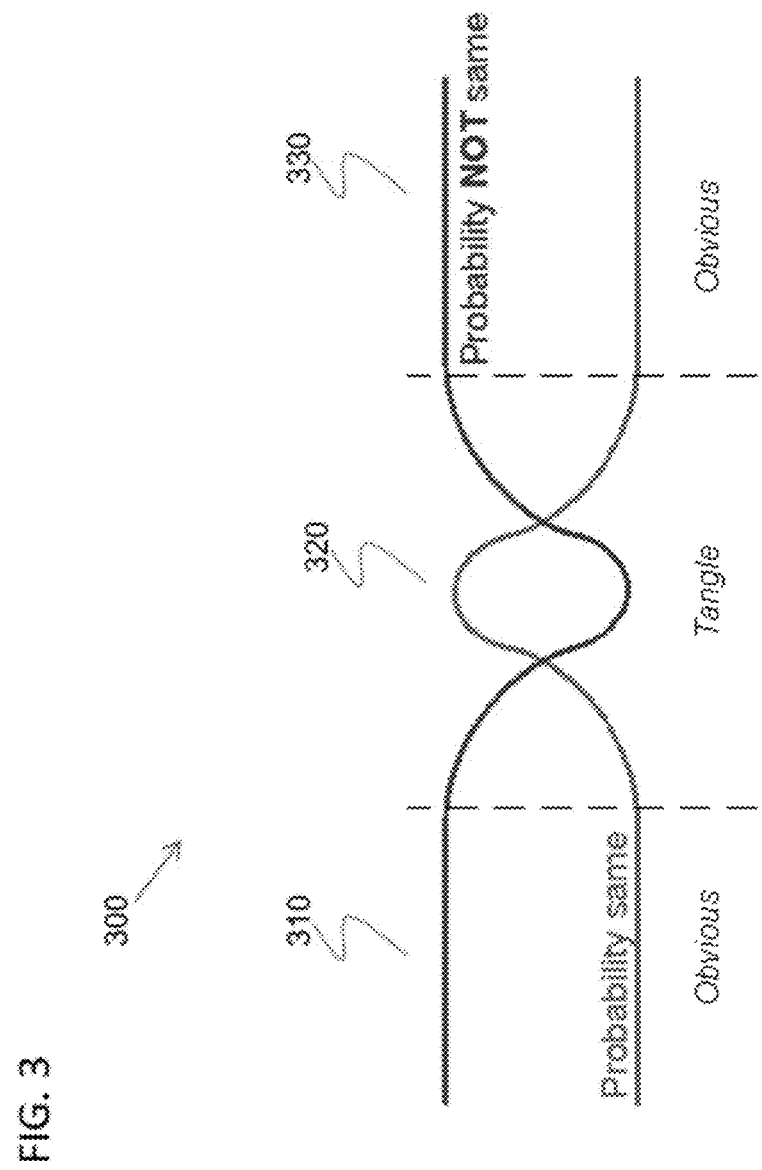
FIG. 3 illustrates an example probability distribution.

As illustrated, for example, in a probability distribution 300 of FIG. 3, probabilities of a code from a first coding scheme matching a code from a second coding scheme provide obvious results when the codes are probably the same 310 and when the codes are probability not the same 330, but a tangled area 320 exists in between. Visual clustering of codes can help unravel the tangled area 320 to understand code matches, for example.

An ontology is a representation of information as a set of concepts within a domain, along with relationships between the concepts. An ontology provides a shared vocabulary that can be used to model a domain. Ontologies and associated metadata provide both challenge and opportunity. A web ontology language (OWL) is a family of knowledge representation languages for authoring ontologies. Data described by an ontology in the OWL family is interpreted as a set of "individuals" and a set of "property assertions" that relate these individuals to each other. An ontology includes a set of axioms that place constraints on sets of individuals (called "classes") and type(s) of relationships permitted between the classes. The axioms provide semantics by allowing systems to infer additional information based on the data explicitly provided.

OWL is built on an eXtensible Markup Language (XML) and a resource description framework (RDF), for example. The RDF is a family of World Wide Web Consortium (W3C) specifications designed as a metadata data model. The RDF can be used for conceptual description and/or modeling of web resource information using a variety of syntax formats. Ontologies represented by OWL can be specialized by use (e.g., SNOMED CT), for example.

Using OWL, a local ontology can be merged with a global ontology, for example. Using a mediator framework, for example, a variety of different systems can communicate and utilize different types of metadata. For example, an electronic medical records (EMR) system, a version controlled file set, and a knowledge and terminology management infrastructure (KTMI) can utilize allergy and picklist metadata. In some examples, a source system provides concepts, and a target system provides receptors. The target system chooses to accept or ignore concepts, for example. Using concept matching and metadata, more than one system can be connected to act on reported outcomes through distributed development.

Certain examples provide systems and methods to visualize and cluster related terminology concepts to facilitate faster concept mappings by users (e.g., medical knowledge workers). Probabilistic matching can be used to match related terminology concepts in ontology-based systems, for example. Matching results can be visualized, such as using a heat map to reveal clustering and/or distribution of concepts and a table or matrix to provide probabilities of mapping codes, terms, concepts, etc., from one scheme to another. For example, an area of "high heat" (e.g., represented as red in a heat map) indicates a strong confidence of coherence between terms (e.g., a match between terms), and an area of "low heat" (e.g., represented as blue in the heat map) indicates a low confidence of correlation or matching (e.g., a plurality of terms has a reasonable chance to match). In certain examples, two coding schemes approximate a distribution pattern between strong confidence fading to lower confidence of matching. Such a "normal probability distribution curve" can be adapted to an M×N matrix model.

Distributed clinical applications involve coordinated metadata. Integration efforts have focused on sharing instance data (e.g., provider X treated patient Y for condition Z). Providers share this instance data with insurers using, for example, an X12 messaging framework and among each other using, for example, an HL7 messaging framework. A similar set of object models and application programming interfaces (APIs) can be used to share/coordinate master data among participants of distributed clinical systems.

Master data object models are a negotiated super set of all known attributes. The API is divided into data sources and data targets. Data sources implement a GET method, for example. Data targets implement three POST methods, for example: 1. Read only comparison report; 2. Pessimistic insert, "add if doesn't already exist"; 3. Optimistic insert, "add and overwrite if already exists". The API is implemented for each transportable class in the object model in each system connector.

Having a framework permits each system to implement a single "plug-in" style connector. Additionally, "plug-in" style tool sets can be developed agnostic of transportable class and systems involved. Tool sets can include, for example: 1. Insert a single instance of a single class from a source to a target; 2. Report differences of a single class between a source and a target; 3. Pessimistic insert all instances of all classes from a source to a target.

In an example, a healthcare institution has several clinical systems for various functions. For each system to contribute data to an enterprise data store, each has an internal representation of metadata (such as a facility at which the system is operating). Manual configuration of each system is both resource intensive and error prone.

In another example, a major system upgrade can involve an old version as a data source is the old version and a new version as a data target. In another example, system state replication involves "best practice" settings distributed and/or problem configurations simulated for debugging. In another example, published third party data sets, such as First Data Bank (FDB) and SNOMED-CT, can be integrated.

Computers lack the fuzzy processing that humans use every day. Data interchanges are done with precise pointers not fuzzy concepts. Standards such as HL7 describe syntax and semantics but do not address meanings of individual terms. Standards such as SNOMED CT standardize terms, but most applications do not create records with those terms. In many instances, such as facility identifiers, it does not make sense to have a standard term. However, each computer system in a federation should use common terms to share data in a meaningful way. This is a major barrier to the use of health information.

In certain examples, two approaches are discussed: one calls for the use of standard vocabularies while the other champions a particular integrated product. Typically, content harmonization remains a manual configuration process. The reliance on standards continues even when the number of standards continues to multiply.

Systems implement business logic to handle exposure to a concept. Each instance of a system is configured. A common API can be developed including a plurality of functions such as read, report, add, overwrite, etc. Each type of content for each type of system is a discrete implementation of the common API. In certain examples, agnostic toolsets are developed for specific use cases, since common functions such as comparison reporting and batch loading can apply regardless of content type. By acknowledging where the variability is, reusable toolsets and connectors can be provided. Implement different API functions results in different toolsets implementing different workflows. Thus, a framework can be provided to manage terminology harmonization across multiple systems.

While standardized vocabularies codify clinical data entry, applications that generate the clinical data rarely map to standards on a one-to-one basis. Some federated clinical systems exchange data using native identifiers, but, currently, informing system X of the native identifiers in system Y is a time consuming manual process.

Existing automated comparison methods rely on transitivity relationships between common standards. E.g. C1=α and C2=α therefore, C1=C2. This requires C1 to match one and only one standard term α, and C2 to match one and only one standard term α. In practice, two competing processes prevent one-to-one mappings. First, standards strive to normalize their concepts to maximize their expressivity and reuse. Second, end user applications strive to de-normalize their concepts to minimize the number of user interactions and chances for error. The failure of vendors to harmonize clinical semantics is a major barrier to growth in healthcare IT.

The National Library of Medicine provides the UMLS Metathesaurus MMTx service. This service accepts natural language text and returns a set of standard terms, each with a score from 0 to 1000. Rather than forcing a rich concept to fit a single standard term, the concept's set of standard terms constitute an encoded signature reflecting the full richness.

Certain examples provide each standard term in a single dimension. A concept's score for the term is then represented as a distance in that dimension. A concept that matches n terms is represented as a point (or vector) in n-dimensional space. A comparison result is a distance between the two points in the combined n-dimensional space.

For example, a concept C1 maps to three terms $\{\alpha, \beta, \gamma\}$. A concept C2 maps to four terms $\{\alpha, \beta, \delta, \epsilon\}$. The matching score is the distance between the two points in a five dimensional Euclidian space, $f(\alpha, \beta, \gamma, \delta, \epsilon)$.

Additionally, term scores can be scaled by Inverse Frequency to help improve distance quality. Common terms such as "of" or "good" are less important than rare terms such as "myocardial infarction". A term's score can be divided by its frequency to determine a frequency-adjusted score.

Further, term scores can be scaled by ontology hierarchical depth to help improve distance quality. Generic terms such as "hypo" or "cardiology" are less important than specific terms such as "laryngopharyngeus". A term's frequency-adjusted score can be multiplied by the term's depth in its ontology hierarchy to generate at the final score used in the above distance calculation. An N-Dimensional Euclidean Distance formula can be represented by:

$$\bar{l} = ((s_{11} - s_{21})^2 + (s_{12} - s_{22})^2 + \ldots + (s_{1n} - s_{2n})^2).$$

Thus, a solution is calculated to match non-standard concepts using advanced natural language processing.

Clinical concepts often have many synonyms that generic string matching algorithms cannot match. Common systems have about one thousand concepts. It takes a human between 15 minutes and an hour to resolve one concept. The algorithm can reduce that to a few seconds with high confidence. The algorithm can match "presents with myocardial infarction" with "patient had a heart attack" in real time (or substantially real time), for example. Using the algorithm, synonyms can be identified to reduce a number of false negatives (e.g., "irregular period" matched with "menstrual irregularity"). The algorithm can also lower the score when the match is semantically incorrect to reduce a number of false positives (e.g., "car assessment" with "cardio assessment"). The algorithm assumes that standardization may never occur and allows individual institutions/departments to tailor their content to their environment and let a computer, rather than a human, handle the mapping.

In certain examples, an algorithm for assigning statistical probabilities favors sensitivity over specificity to identify many possible matches. Parameters of an example algorithm can be adjusted to be more or less specific and, therefore, more or less inclusive, for example.

An M×N probability matrix provides a computerized system with a framework for scoring at any of a variety of levels of granularity. An indication of a possible match between concepts is represented within the M×N matrix. In certain examples, a Euclidian distance formula can be applied in conjunction with the M×N matrix using linear algebra (e.g., the mathematics of matrices) to define a transformation from one vector to another. In certain examples, an M×N matrix can be used for code system to code system comparison, concept to concept comparison, and/or property to property comparison.

In an example, healthcare terminology provider data is analyzed using an algorithm that ranks criteria including the granularity of a medical term (e.g., simpler words have a smaller number of letters), the popularity of a term (e.g., how often is the term used by the organization), and the relationship to similar terms (informed by semantic proximity, other medical publications, and external dictionaries, for example). This analysis results in one or more proposals of where to place the provider's data and representations of data in a controlled medical vocabulary that spans organizations. Since the provider data is mapped to standards, interoperability and the use of localized terms are both possible.

Medical terminology vocabularies often include overlapping information. In an example, similarities and overlapping elements between vocabularies are identified. A confidence level of the similarity between the elements can then be provided. Rather than requiring a significant amount of human resources to review each term, often without regard to applicable standards, some review can be automated to reduce the amount of analysis left for manual human review.

In an example, a controlled medical vocabulary (CMV) is created for a clinical system and/or clinical application that covers a variety of terms (e.g., everything from problem lists to allergies to drugs). The terminology is transferred to an "inbox" with one or more proposed mappings using SNOMED, ICD9, ICD10, LOINC, Digital Imaging and Communications in Medicine (DICOM), American College of Radiology (ACR) Index of Radiological Diagnoses, American National Standards Institute (ANSI) identifiers, etc., and/or into a visual mapping tool where a user can see those mappings in more of a visual way to help a person developing a CMV.

A CMV is a capability of a computer-based patient record (CPR) system. Other CPR core capabilities include clinical documentation and data capture, clinical display including a clinical dashboard, a clinical workflow, order management including physician order entry, a clinical data repository (CDR), clinical decision support (CDS), privacy support, and interoperability connectivity. A CMV supports medically relevant concepts, terms, codes and relationships.

CMV services can be delivered using a vocabulary server that provides access to a set of CMV functions as a series of application programming interfaces (APIs). This approach makes the CMV accessible to any software component in the CPR or its environment that uses such services. In many cases, a set of terminologies such as SNOMED, ICD-9, ICD-10, and Current Procedural Terminology-Fourth Edition (CPT-4), including cross maps between their respective terms, is included. Using the CMV and vocabulary server, vocabulary services can be provided to subsystems of a core CPR system as well as other subsystems in the CPR environment. The CMV and vocabulary server can provide information concerning a medical term or concept to an executing application and can also accept terminology updates.

Using a CMV, CPR systems can understand and more intelligently process medical information while continuing to store that information in a form (e.g., medical terms) that permits humans to interact with the same data. In an example, a user can enter a query against information in a data warehouse (which has received its data from the CDR) asking to retrieve cases corresponding to certain search terms. If the CMV has been used to classify the information in the data warehouse, then the query should successfully retrieve all relevant cases including cases using equivalent terminology. The CMV can provide a comprehensive answer by using a search algorithm to explore its semantic network, for example.

In an example, limited CMV capabilities exist in a CPR system. For example, CMV capabilities allow mapping terms into canonical terms, generating billing codes, etc. These mappings can be hard-coded into applications, for example. In such environments, a CPR system supports generation of standard code sets such as ICD-9 and CPT-4.

In an example, the CMV exists as an architecturally separate component in the CPR. The CMV can be used to explicitly manage concepts, terms, and relationships, as well as cross-mapping these concepts, terms, and relationships to standardized encoding schemes. Applications such as clinical decision support and clinical workflow can have a significant degree of CMV interaction. An API for a vocabulary server supports the vocabulary needs of the clinical decision support and clinical workflow as well as related applications and/or components. The CMV/vocabulary server combination can support tools to enable terminologies to be updated and to resolve resulting conflicts. Proposed CMV content can be compared to current CMV content, establish semantic consistency in the new content, and track changes made to the CMV.

In an example, a vocabulary server supports interacting vocabulary needs of the CPR environment. The vocabulary server permits users to interactively explore the vocabulary's semantic network, maintain local vocabulary variations, incorporate new content, handle versioning issues, and provide real-time (or substantially real-time) responses to queries for vocabulary services. To support a full spectrum of CPR functions, the CMV provides "decompositional completeness". That is, the CMV contains atomic representations of pre-coordinated terms contained in the CMV. Thus, if the CMV includes a pre-coordinated term or phrase including multiple elements, then the CMV includes primitive terms for each of those elements. The CMV also includes a convention or rule that describes how to use the primitive terms for each of the elements to create a post-coordinated term having the identical semantic content as the pre-coordinated term. A CMV that provides decompositional completeness enables applications, such as medical natural language processing applications, to function properly despite the existence of pre-coordinated terms that differ in form from the specific terms that can be created by a CPR system user (e.g., "myocardial infarction" versus "heart attack"). The CMV can also support the clinical workflow and clinical decision support capabilities of the CPR system. CMV can be used to support evidence-based medicine (EBM) functions such as automated care guideline protocols. The CMV also includes support for manual vocabulary updates and resolution of vocabulary semantic conflicts.

In an example, the CMV and vocabulary server support a full range of real-time vocabulary services, as well as being able to receive automated updates from vocabulary authorities. The CMV supports many industry-standard coding systems. The vocabulary server management system supports automated integrity checking of the CMV's semantic network and can provide automated support for EBM functions. The CMV can be combined with capabilities such as clinical workflow, CDS, EBM, natural language processing, and continuous speech recognition to provide an environment where a variety of clinical input (e.g., typing, speech, menu picks, and external documents) are incorporated into the CPR system's functions. The CMV can work in conjunction with clinical workflow and CDS to help provide knowledge management within the CPR system.

In an example, a mapping between external terminologies and use of text-based analysis to provide additional meaning and presentations of medical codes and terms by supplementing the data with localized clinical content is automated. The example process can include the following: 1) An initial CMV is created by cloning sections of external terminologies based on healthcare data domain (e.g., LOINC for laboratory terminology, CPT for medical procedures, etc). The structures (e.g., relationships, concepts, and terms) of the standard terminologies are retained where applicable. Mappings between the CMV and publicly available mappings (e.g., ICD-9 to ICD-10, SNOMED to CPT, etc.) are then used to create a web of related data. The web of data includes both direct (e.g., equivalent) and indirect mappings (e.g., is broader than, is narrower than). 2) Rules are created based on the mappings to determine how to handle changes to the source terminology. For example, when a new term is added by a third party organization, then the mapping for sister terms can specify to automatically propagate 'additions' or put them into proposed status for review. 3) In addition to creating a CMV based on standard vocabularies, customer presentations and mappings can also be included. To create such a CMV, a healthcare organization aggregates its clinical content including nursing, physician, and administrative documents, for example. Much of this data is currently collected in an unstructured mechanism via comment and note fields and thus very difficult to maintain in a structured terminology system. 4) This unstructured clinical content is then run through a text analyzer and extraction tool to organize the information based on synonyms, abbreviations, and relevance to existing source terminologies, for example. 5) Source terminologies and medical dictionaries are used to augment the intelligence of the text analyzer. 6) Proposed terms and synonyms are extracted based on linguistic and probabilistic algorithms. Proposals are put into a queue for a terminology engineer to validate and promote to the controlled medical vocabulary, for example. 7) Local synonyms and presentations based on the unstructured data analysis can be automatically put into a proposed queue to be added to the CMV.

In an example, controlled medical terminology services and modeling and management tools are used to provide advanced analytics, real-time decision support, and business intelligence through use of structured, coded data. CMV systems store high quality, computationally comparable, reliable, and reusable data to support such services. Additionally, internal and external interoperability of systems, processes, and data can be provided to reduce costs incurred due to redundant and disparate data definition, storage, and maintenance and to promote national and international interoperability by sharing terminology with the healthcare community at large, for example.

Figure 4:
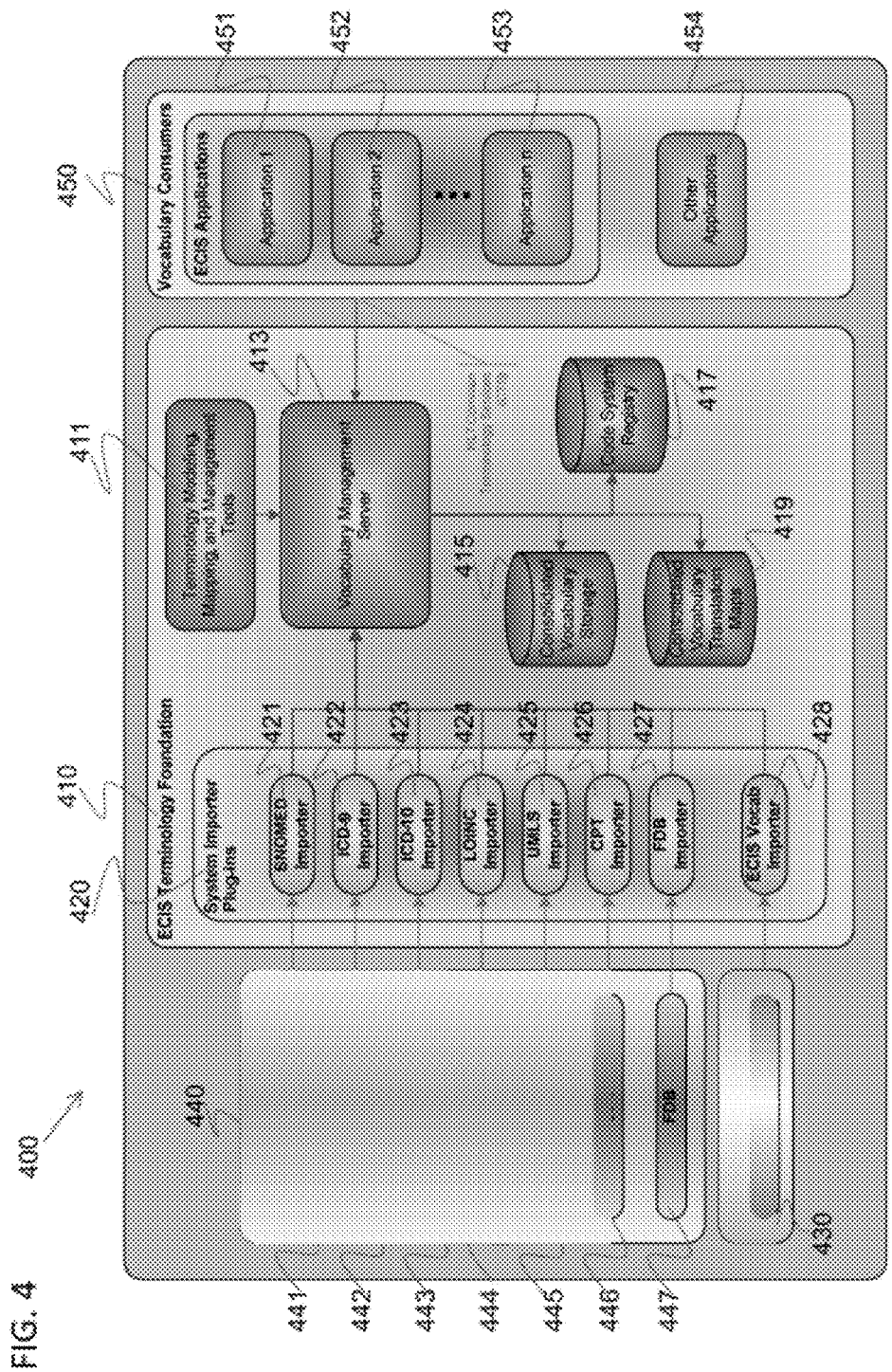
FIG. 4 illustrates an example controlled medical vocabulary (CMV) system.

As shown in FIG. 4, for example, a controlled medical vocabulary (CMV) system 100 includes a terminology foundation subsystem 410, a common vocabulary 430, one or more external vocabularies 440, and one or more vocabulary consumers 450.

The terminology foundation subsystem 410 includes modeling and management tools and common terminology services for code mapping, browsing, and querying services. For example, the terminology foundation subsystem 410 includes terminology modeling, mapping, and management tools 411, a vocabulary management server 413, a consolidated vocabulary storage 415, a code system registry 417, and consolidated vocabulary translation maps 419. The terminology foundation subsystem 410 also includes one or more system importer plug-ins 420. The system importer plug-ins 420 can include one or more of a SNOMED importer 421, an ICD-9 importer 422, an ICD-10 importer 423, a LOINC importer 424, a Unified Medical Language System (UMLS) importer 425, a CPT importer 426, a First Data Bank (FDB) importer 427, and a common vocabulary importer 428.

External vocabulary(ies) 440 can include a SNOMED-CT vocabulary 441, an ICD-9 vocabulary 442, and ICD-10 vocabulary 443, a LOINC vocabulary 444, a UMLS vocabulary 445, a CPT vocabulary 446, an FDB vocabulary 447, etc.

Vocabulary consumer(s) 450 can include one or more applications 451-454. Vocabulary consumers 450 communicate with the terminology foundation subsystem 410 using technology services, such as HL7 Common Technology Services (CTS) 460.

Using the system importer 420 of the terminology foundation subsystem 410, external code systems (e.g., SNOMED, LOINC, CPT, ICD-9, ICD-10, etc.) can be loaded into a consolidated repository. Modeling tools 411 allow informaticists to create, modify, map, and/or manage vocabulary concepts. Data storage and services 413 are used to store and retrieve external code systems 417, translation maps 419, and a controlled medical vocabulary 415. Browsing, code mapping, and runtime services based on the HL7's Common Terminology Services 460 specification support a standards-based controlled medical vocabulary. Versioning, life cycle management, dependency resolution, and packaging services support publishing of terminology across environments.

Figure 5:
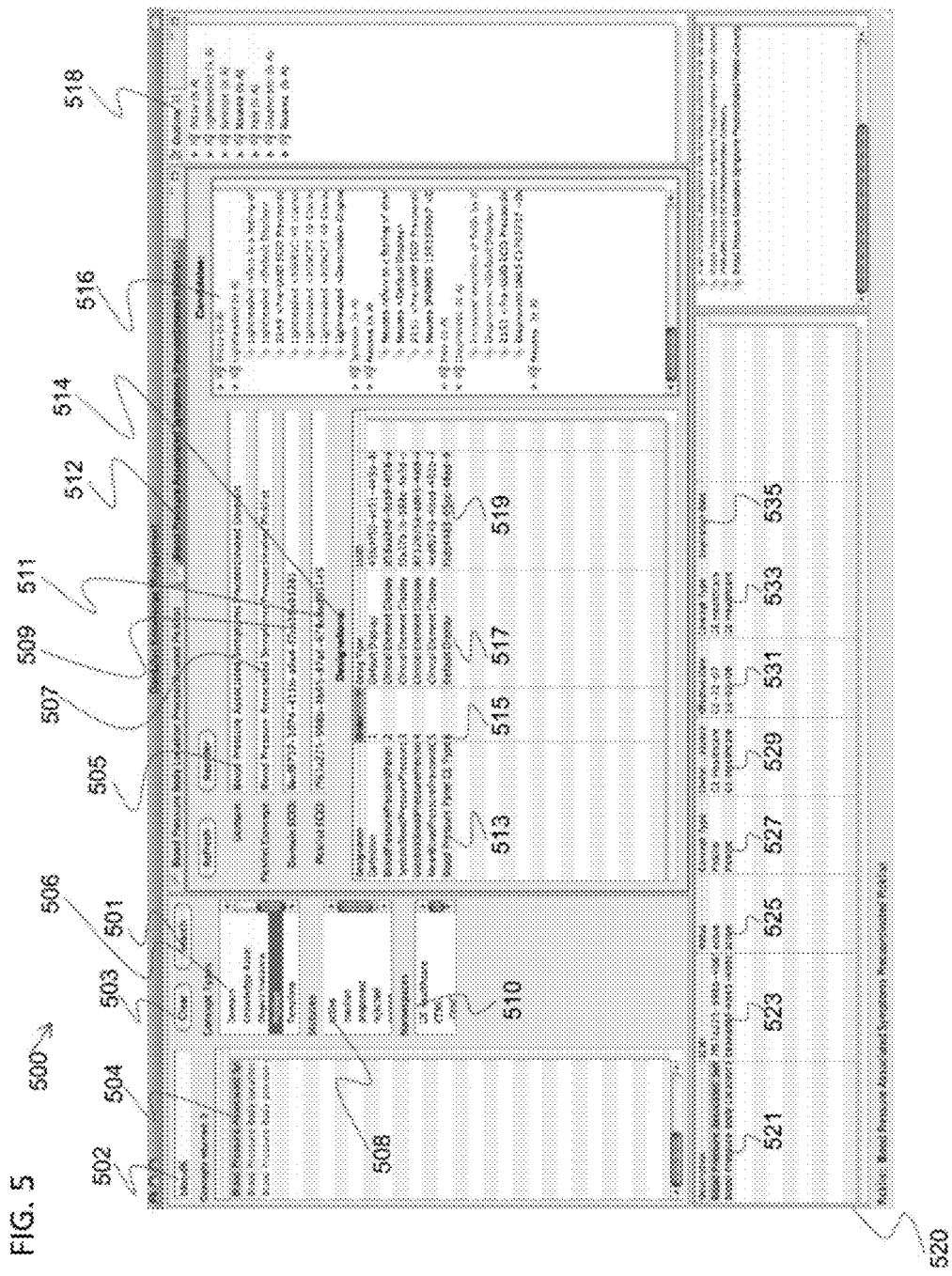
FIG. 5 illustrates an example terminology mapping tool interface.

As illustrated, for example, in FIG. 5, terminology mapping tools load controlled vocabulary content (e.g., LOINC, SNOMED, ICD-10, etc.) from standards organizations and allow informaticists to create, modify, map, and/or manage vocabulary concepts. Using a knowledge management interface 500, shown, for example, in FIG. 5, a search input 502 returns one or more resulting vocabulary concepts 504. The search input 502 can be executed or cleared using buttons 501, 503, respectively. Search results 504 can be filtered and/or sorted by one or more additional criteria such as concept type 506, status 508, namespace/owner 510, etc. Selecting a concept in the search results 504 displays information regarding that concept in a display area such as the picklist 512 shown in FIG. 5. Within the picklist 512, information relating to the selected concept 504, such as domain 505, picklist concept 507, domain enterprise concept identifier (ECID) 509, and picklist ECID 511, is displayed for user review, input, and/or modification. Designations 514 within the selected concept 504 are provided, including designation name 513, order 515, type 517, and universally unique identifier (UUID) 519, for example. Additionally, one or more candidate symptoms 516 are provided including detail regarding each symptom. These symptoms are also displayed in an outline 518.

A set of selected concepts 520 is also provided at the bottom of the interface 500. The set 520 summarizes the description 521, ECID 523, status 525, concept type 527, owner/namespace 529, effective date 531, concept type 533, and expiration date 535 for each concept. The interface 500 also provides notes 522 regarding a selected concept.

For example, as depicted in the interface 500 of FIG. 5, a user can search 502 for vocabulary concept(s) involving words starting with "blood." A user can select a concept type 506, such as a picklist, a status 508, such as active, and a namespace 510, such as GE Healthcare, to refine the search results. A returned concept 504 can be selected to populate the domain 505, picklist concept 507, domain ECID 509, and picklist ECID 511, for example. For the selected concept picklist, designation information 514 including designation name 513 (e.g., blood pressure panel), order number 515 (e.g., 1 through 6), designation type 517 (e.g., clinical element display, default display, etc.), and UUID 519 can be provided. One or more candidate symptoms 516, such as dizziness, lightheadedness, nausea, etc., can be selected and also provided in outline 518 form. A set 520 of selected concepts 504, such as one or more blood pressure concepts, provides a summary of ECID 523, status 525, concept type 527, owner/namespace 529, effective date 531, concept type 533, and/or expiration date 535.

Concepts from a controlled terminology may not be sufficiently meaningful without a clinical structure to provide context. With a large number of equally correct ways to say the same thing, understanding a desired meaning becomes unreasonably burdensome. Clinical Element Models (CEMs) can be utilized as the basis to model, store, and/or retrieve dynamically changing clinical concepts and information.

A CEM is a data structure that represents a unit of medical information, including its interrelated components. CEMs enable content-driven systems development so that healthcare delivery can be documented consistently, measured reliably, and improved continuously over time and across patients, providers, care settings, and applications.

Figure 6:
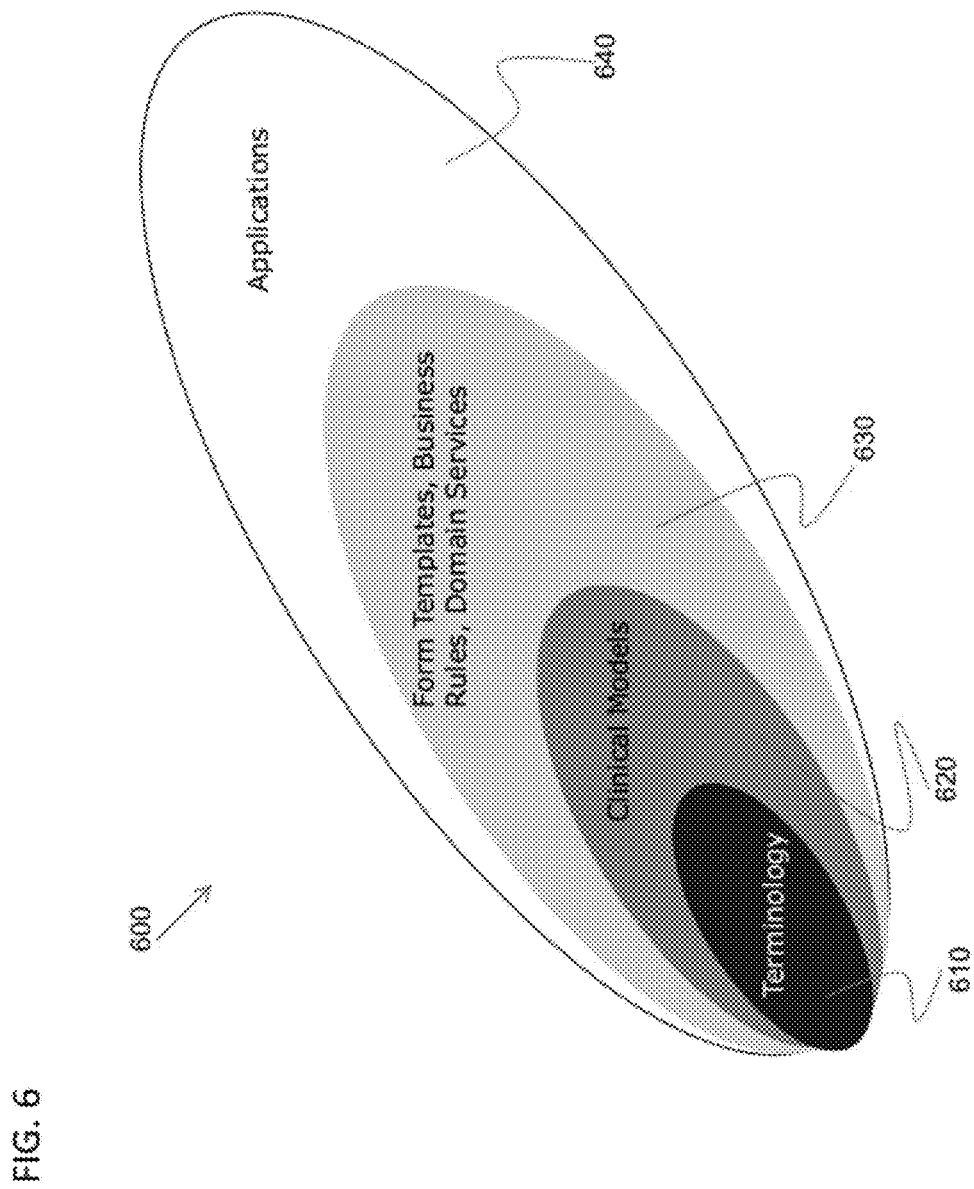
FIG. 6 illustrates an example coded, controlled medical vocabulary that can serve as a basis for understanding clinical data.

A controlled medical vocabulary and clinical models form the basis for a content driven system that supports dynamic data, workflows, and/or decision support. As illustrated, for example, in FIG. 6, a terminology 610 provides a coded, controlled medical vocabulary that can serve as a basis for understanding clinical data. One or more clinical models 620 provide detailed clinical element models (CEMs) representing information models bound to the terminology 610. One or more form templates, business rules, and/or domain services 630 provide reusable elements that add context regarding how an application would utilize content. The form templates, business rules, and/or domain services 630 are consumers of the clinical models 620 and terminology 610. One or more applications 640 provide content-driven applications whose behavior is driven by dynamic templates and rules based on the form templates, rules, and/or services 630, clinical models 620, and terminology 610.

As used herein, several components provide information and functionality for terminology management. Example definitions of these components are provided below.

A code system is a resource that makes assertions about a collection of concepts, where the concepts are uniquely identified by concept identifiers and represented by designations. Code systems are often referred to as terminologies, vocabularies, coding schemes, and/or code sets. A code system can be a terminology (e.g., LOINC), a vocabulary (e.g., SNOMED), a classification (e.g., ICD-9 CM), a thesaurus (e.g., MeSH), an ontology (e.g., FMA), or just a list of codes (e.g., HL7 code systems). A code system can include concept relations where concepts are related by certain relationships, or a code system may just contain a flat list of codes with their designations, for example. A given code resolves to one meaning within the code system.

A concept is description of a unit of knowledge created by a combination of concept properties and concept relations within the context of a code system. A concept identifier is a numeric or alphabetic symbol that identifies a concept within the context of a code system. A concept identifier is often referred to as an entryCode (e.g., in Mayo Clinic's Lexical Grid or LexGrid framework for representing, storing, and querying biomedical terminologies) and concept code (e.g., in HL7, CTS II), or just a code. The concept identifier can be meaningful when it is related to the concept properties of the concept, such as mnemonic codes, hierarchical codes, etc. The concept identifier can be non-meaningful when it is not related the concept properties, such as sequential id, UUID, etc.

A qualified concept code is a combination of a code system identifier and a concept identifier. A qualified concept code provides a globally unique name for the description and, by proxy, the referenced "unit of knowledge". HL7 uses ISO Object Identifiers (OIDs) as code system identifiers. LexGrid uses Universal Resource Identifiers (URIs). The current KTMI system uses DCE UUIDs for both code system identifiers and locally authored concept identifiers. Note that both OIDs and UUIDs can be transformed into URI's by prefixing them with "urn:oid:" and "urn:uuid:" respectively.

A concept property is an abstraction of a characteristic of a concept for defining and identifying the concept. A designation is a textual concept property that can be used to represent the intended meaning of a concept in certain usage context. A designation is often referred to as presentation (LexGrid), representation, term (ISO 17115), name (HL7), etc. A definition is a concept property that provides a textual definition of the concept.

A relationship type is a binary predicate that, when asserted to be true between two concepts, asserts that a corresponding external relationship applies between the classes and/or instances described by the concepts. A relationship type is referred to as an association in LexGrid, although the LexGrid model confuses the type (association as entity) and the set of assertions (association container for association-Source).

A relationship is an assertion of an association that pertains between two or more concepts through hierarchical, associative, sequential, temporal or causal relationship types. Concept relation is often referred to as association (e.g., LexGrid), relation, concept relationship (e.g., CTS II), relationship, hierarchy. Association in LexGrid allows the source and target concepts to be from different code systems.

A usage context is a set of conditions that need to be fulfilled before a terminological component (includes concept property, designation, relationship, picklist, concept map) is eligible for usage. Usage context is often referred to as context of use, context, and/or application context. Usage context includes application contexts, clinical contexts, user contexts, patient contexts, etc. The set of conditions can be pre-coordinated into a description of an environment, or stays as multi-parameter conditions. The HL7 usage context is limited to the conditions in which a Value Set (See Value Set section) can be used.

A picklist is an ordered list of designations where the concepts represented by the designations are drawn from the same value set. Since the value sets in LexGrid, HL7 and CTS II are independent of specific code system, a picklist can also be generated with values from multiple code systems, for example.

A concept map is a set of rules for transforming a concept from one code system to a concept in another code system. A concept map is often referred to as concept mapping, or just mapping, association (e.g., LexGrid).

A value set definition is a set of rules that, when applied to a code system version, results in a list of qualified concept codes. A value set definition can be represented by a simple list of one or more concept codes or by a formula such as "all concept codes in a specific namespace", "all concept codes that are the target or source of a concept relationship", "all concept codes referenced by another value domain definition", etc.

A value set is a combination of a set of qualified concept codes resolved from value set definition and the corresponding values that represent the qualified concept codes in the context of a specific message or database. Value sets are frequently created algorithmically. Common value set algorithms include the specification that the concept identifier will represent the qualified concept code, that the preferred designation will represent the qualified concept, and/or that the value of a particular property will represent the value, for example.

Figure 7:
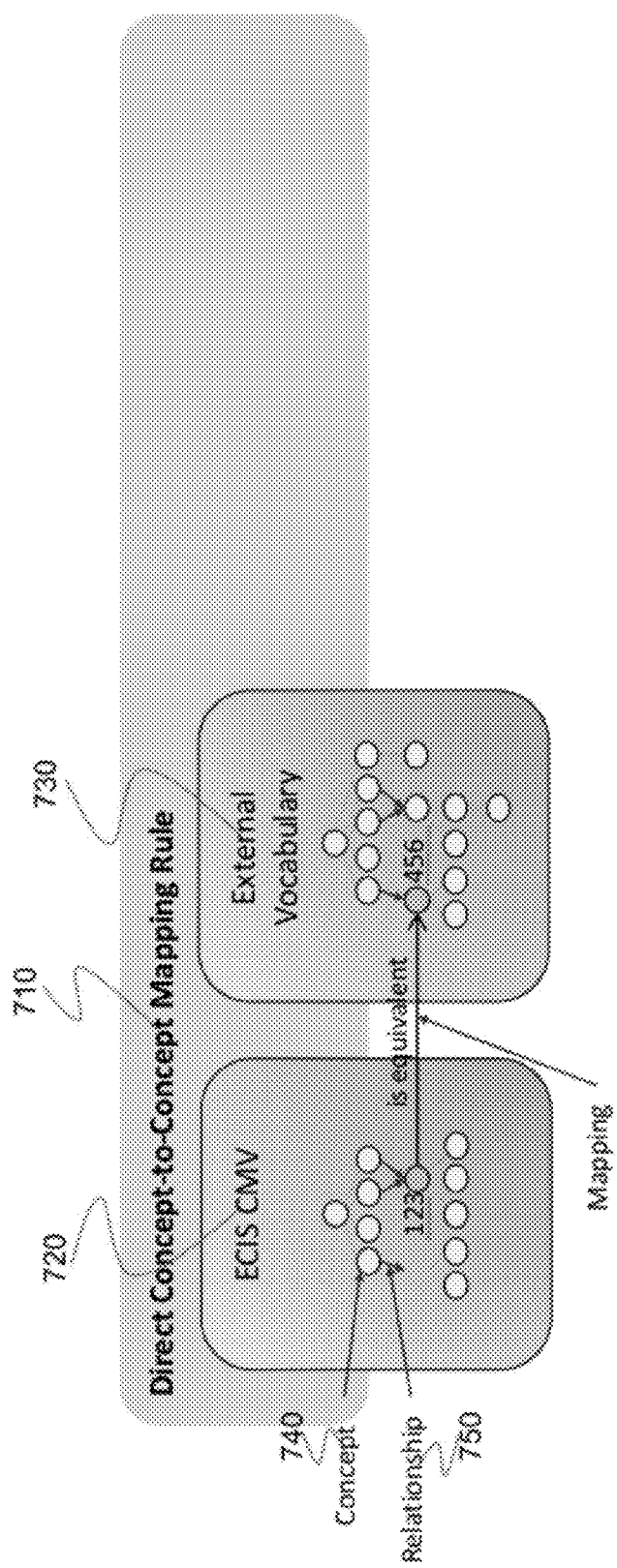
FIG. 7 depicts an example direct concept-to-concept mapping rule applied between a clinical information system CMV and an external vocabulary.

In an example, concepts are automatically mapped. For example, as depicted in FIG. 7, a direct concept-to-concept mapping rule 710 can be applied between a clinical information system CMV 720 (e.g., GE Clinical Knowledge System (CKS) controlled medical vocabulary) and an external vocabulary 730 (e.g., RxNorm, Snomed CT, LOINC, ICD-9, etc.). In the example of FIG. 7, a concept 123 is equivalent to a concept 456. As illustrated in the example of FIG. 7, each concept can be related to one or more concepts 740 by relationships 750. Since the concept 123 is automatically identified as equivalent to the concept 756, by rule, changes to concept 456 in subsequent versions of the external vocabulary 730 are identified and automatically proposed in the CIS CMV 720.

Figure 8:
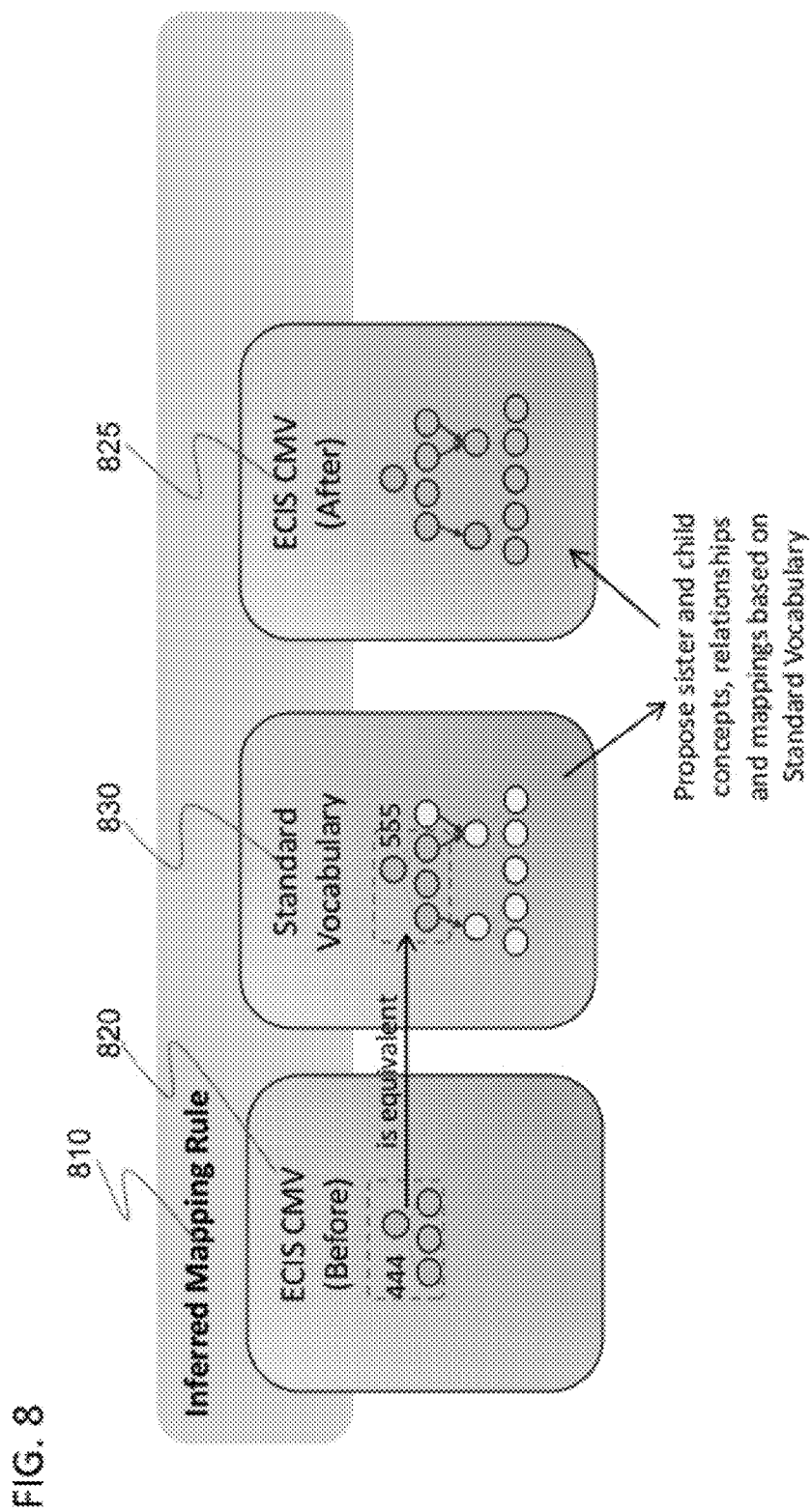
FIG. 8 depicts an example inferred mapping applied to a CMV and a standard vocabulary to generate an updated, inferred CMV mapping.

Alternatively and/or in addition, an inferred mapping rule can be applied to concepts. As illustrated, for example, in FIG. 8, an inferred mapping 810 is applied to an ECIS CMV 820 and a standard vocabulary 830 to generate an updated, inferred ECIS CMV mapping 825. In the example of FIG. 8, a concept 444 is equivalent to a concept 555. Using the inferred mapping rule 810, sister and child concepts, relationships, and mappings are proposed based on the standard vocabulary 830. By rule 810, sister and child concepts in the ECIS CMV 820, 825 are automatically proposed based on the standard vocabulary 830.

Figure 9:
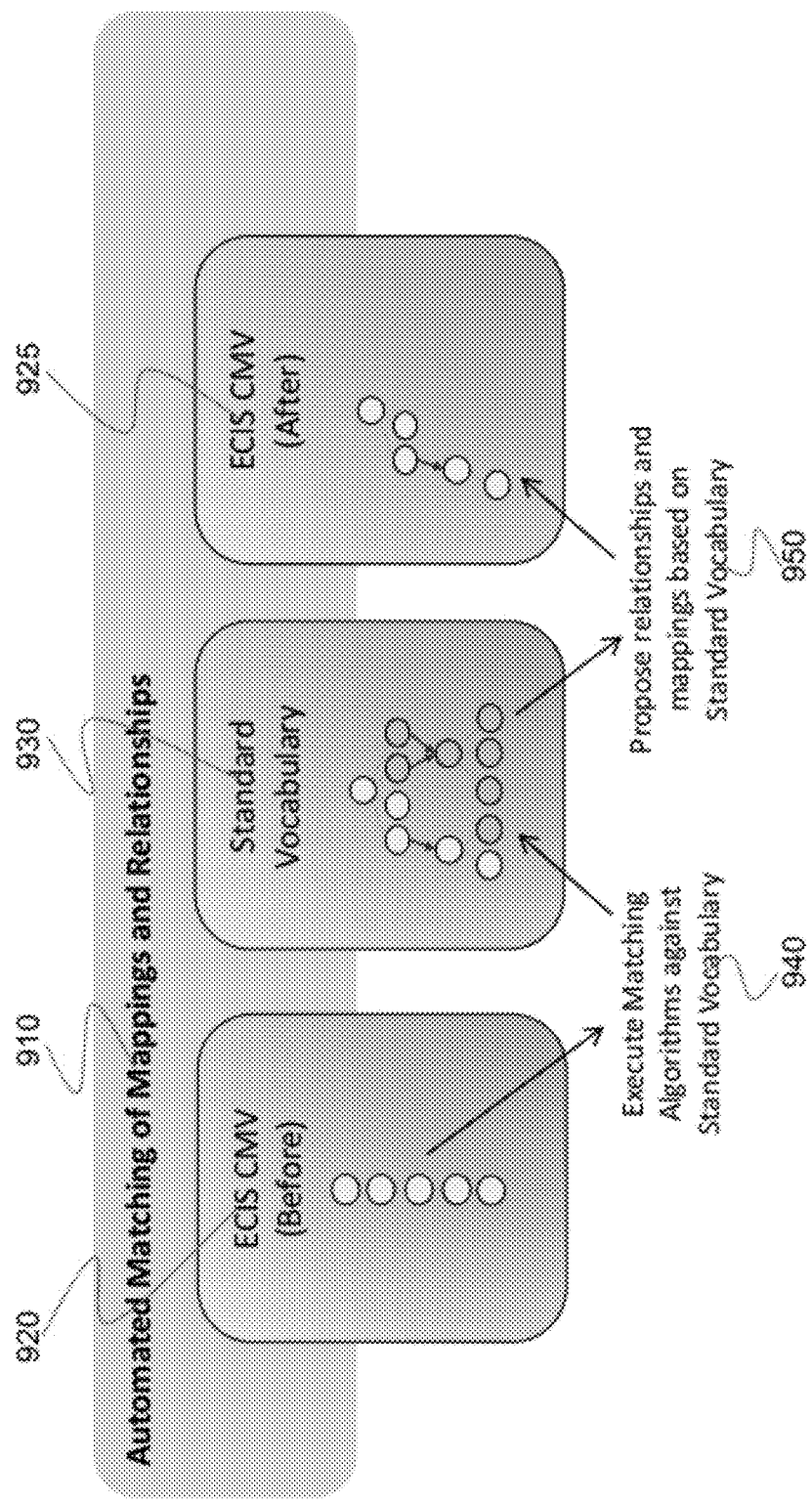
FIG. 9 depicts an example automated matching of mapping and relationships applied to a CMV and a standard vocabulary to generate an updated CMV mapping.

As illustrated in example FIG. 9, relationships between concepts can be inferred. Using an automated matching of mappings and relationships 910, an ECIS CMV 920 and a standard vocabulary 930 can generate an updated ECIS CMV 925. Matching algorithms 940 can be applied to the ECIS CMV 920 based on the standard vocabulary 930. Then relationships and mappings for the updated CMV 925 can be proposed 950 based on the standard vocabulary 930.

Figure 10:
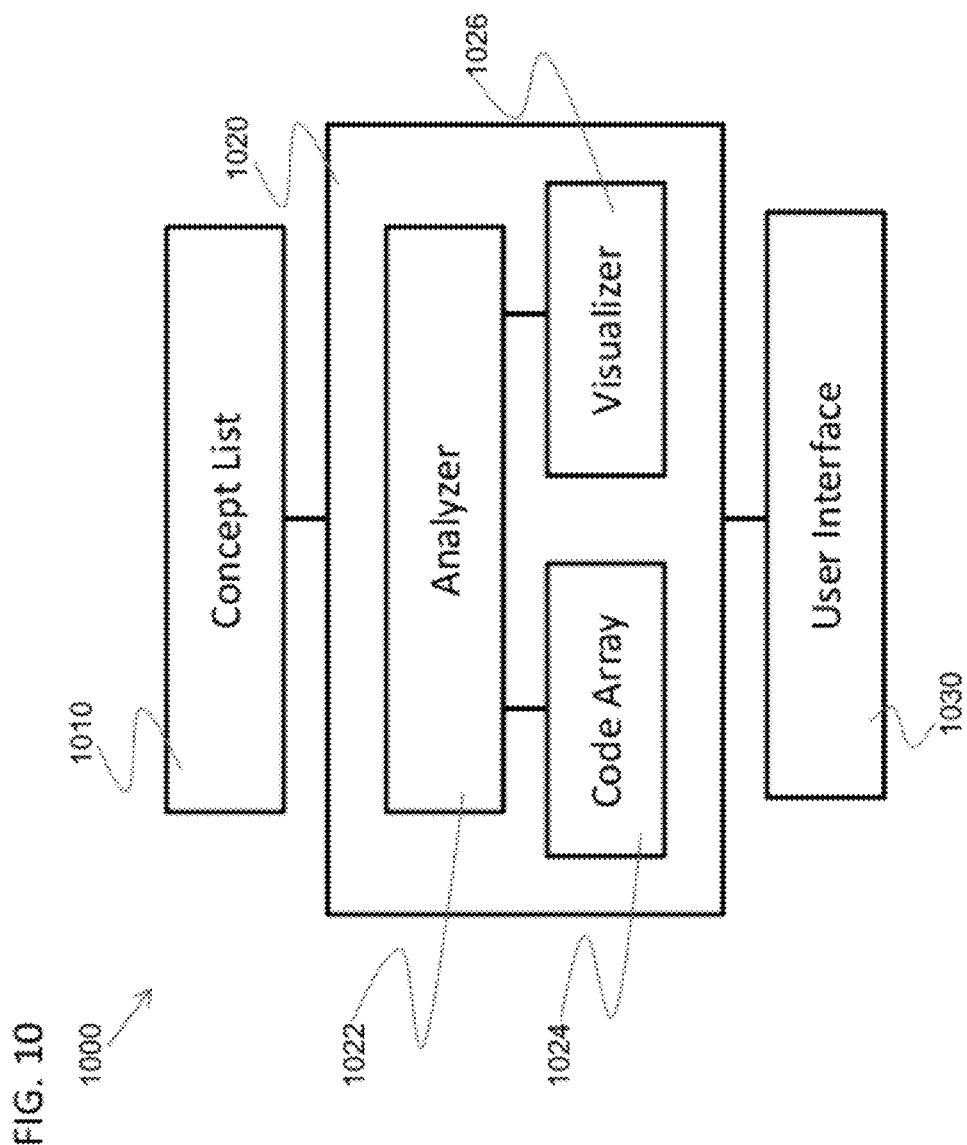
FIG. 10 illustrates an example code scheme mapping system.

FIG. 10 illustrates an example code scheme mapping system 1000 including a concept list 1010, a code mapper 1020, and a user interface 1030. The concept list 1010 of the example of FIG. 10 includes a list of coded concepts according to two or more different coding schemes. In the example, the mapper 1020 includes an analyzer 1022, a code array 1024, and a visualizer 1026. In FIG. 10, the concept list 1010 is provided to the code mapper 1020 which provides output to and accepts input from the user interface 1030.

The coded concepts found in the concept list 1010 are provided to the analyzer 1022. The analyzer 1022 determines probabilistic matches between concepts from different coding schemes in the concept list 1010. One or more probabilistic matching algorithms can be leveraged to match related terminology concepts, for example. Matching can be facilitated according to an understanding of type, category, and/or other criteria, for example. Words, synonyms, codes, etc., can be searched in respective coding schemes to identify potential match(es), and probabilities can be assigned to those matches, for example.

In certain examples, probabilistic matching can be facilitated using a language such as OWL to represent or model ontologies. Using a defined model, a match can be made between terms or concepts. Using probability, a probability that two concepts match can be represented as a product of a number of terms involved and is based on the model, for example.

The analyzer 1022 outputs a code array 1024, such as a matrix, table, and/or other array of "matched" codes. The array 1024 can include a matrix of potentially matching codes from two or more schemes and a probability and/or other indication of the likelihood of a match, for example.

The analyzer 1022 also provides coded concepts from the concept list 1010 to the visualizer 1026. The visualizer 1026 depicts coded concepts from the concept list 1010 in a visual format, such as a color-coded or "heat" map for user review. Concepts can be depicted in a visual (e.g., graphical) format via the visualizer 1026 and using the user interface 1030 that illustrates potential match(es) among concepts based on, for example, proximity between the concepts on the display.

Figure 11:
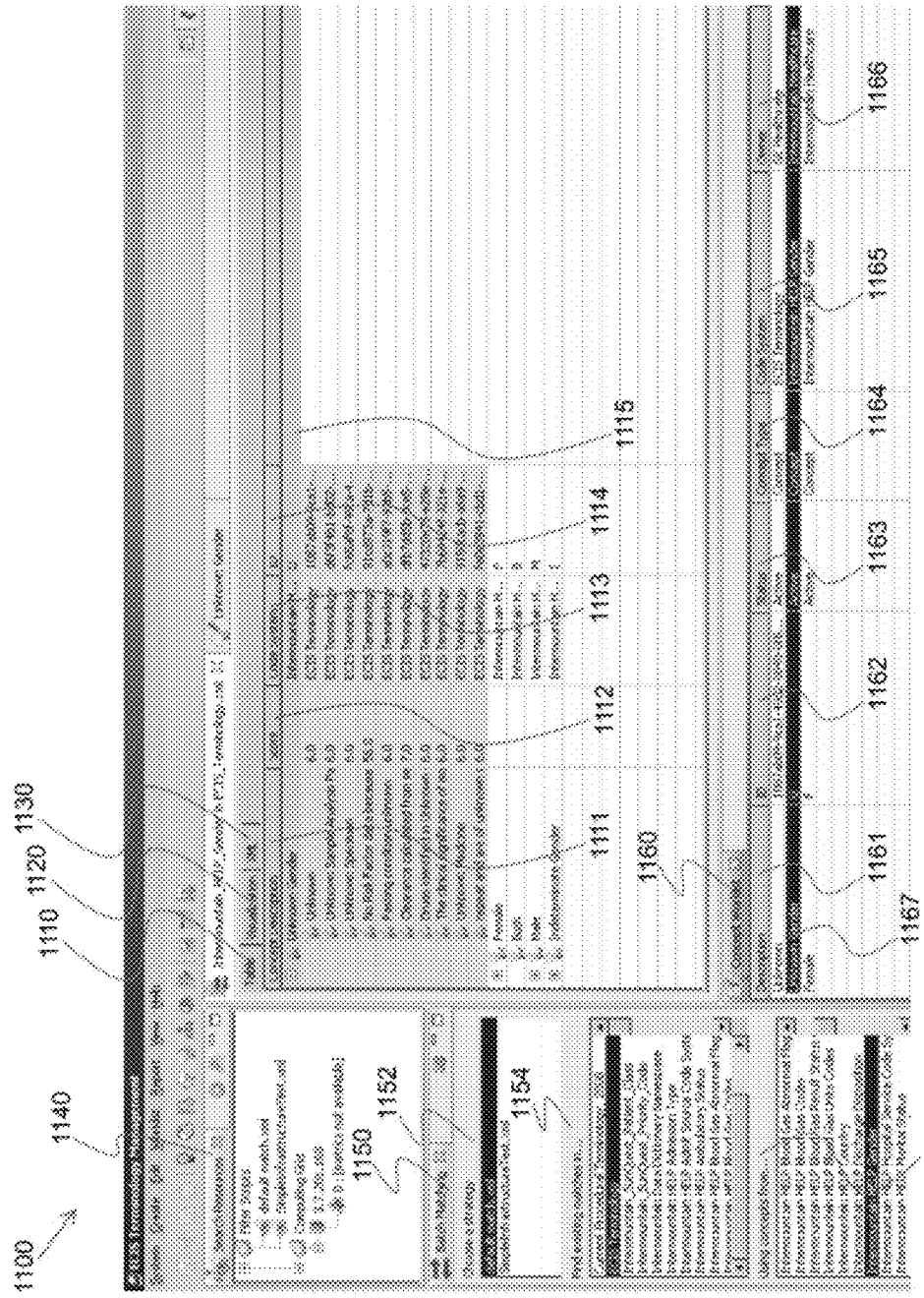
FIG. 11 illustrates an example user interface for review of proposed code matches.

Using the code array 1024 and the visualize 1026 output via the user interface 1030, a user can review proposed code matches and approve and/or correct the matches. For example, as shown in FIG. 11, an interface 1100 is provided to a user. The example interface 1100 includes a table view 1110, a visualization view 1120, and an XML source view 1130.

The interface 1100 allows a user to search resources 1140 and perform batch matching 1150, for example. In batch matching 1150, a user can select a matching strategy 1152 to find existing matches in a selected terminology 1154 using concepts from a selected code system 1156, for example.

The interface 1100 can also provide the user with a concept worklist 1160. In the example worklist 1160 of FIG. 11, the user can review a description 1161, an identifier 1162, a status 1163, a concept type 1164, a code system 1165, and an owner 1166 for each concept in the worklist 1160. From the concept worklist 1160, a user can select (e.g., by double clicking) a concept 1167 to open that concept in an editor, for example.

The table view 1110 of the example interface 1100 of FIG. 11 provides a list of concepts for user review and selection. Concepts are identified by concept description 1111, matching score 1112, code system 1113, and identifier 1114, for example. By selecting a concept 1115 in the table view 1110, the concept 1115 (e.g., "Unknown Gender") can be expanded to show its options or variants. Additionally, by selecting (e.g., by double clicking) a concept 1115 in the table view 1110 of the example of FIG. 11, a user can add the concept 1115 to the concept worklist 1160.

Figure 12:
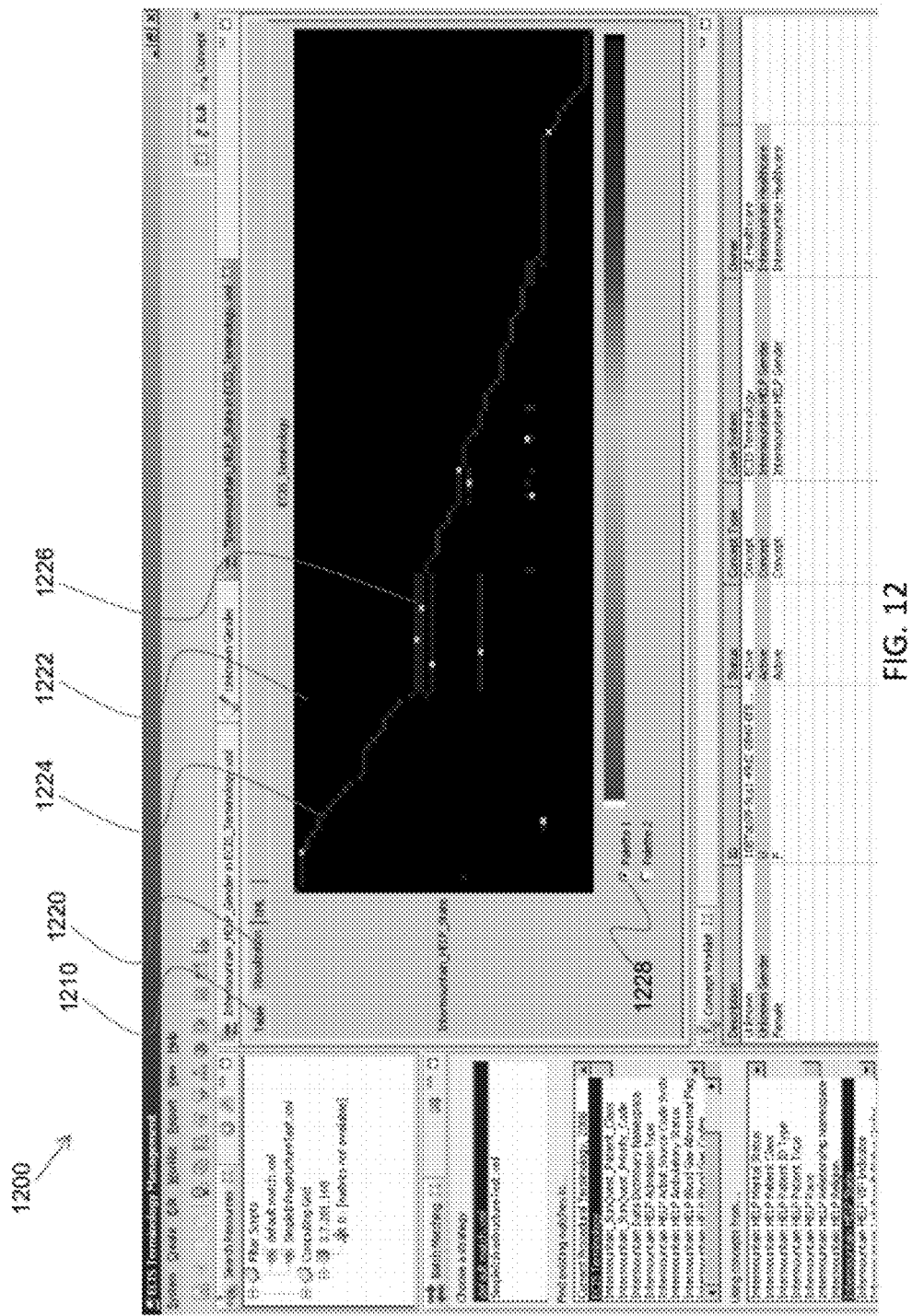
FIG. 12 illustrates an example interface showing a visualization view of concept matching data.

FIG. 12 illustrates an example interface 1200 showing a visualization view 1220 of concept matching data. A user can switch between a table view 1210 and a visualization view 1220 of the data without delay (at least without significant delay). The visualization view 1220 of the example of FIG. 12 provides a visual (e.g., heat map) depiction 1222 of correlations between state names useful in a state comparison. The visual representation 1222 can be used to graphically highlight differences or similarities in concept terms. For example, as shown in the visual representation 1222 of the example interface 1200, an area of tight correlation 1224 suggests that the corresponding terms are unique. Conversely, an area of clustering 1226 around a word (e.g., states having the word "New" such as New York, New Jersey, New Mexico) suggests an area for further review to determine a match. In the example of FIG. 12, a user can select a color palette 1228 with which to visually depict clusters and/or lack of clusters among terms in the visualization representation 1222.

Figure 13:
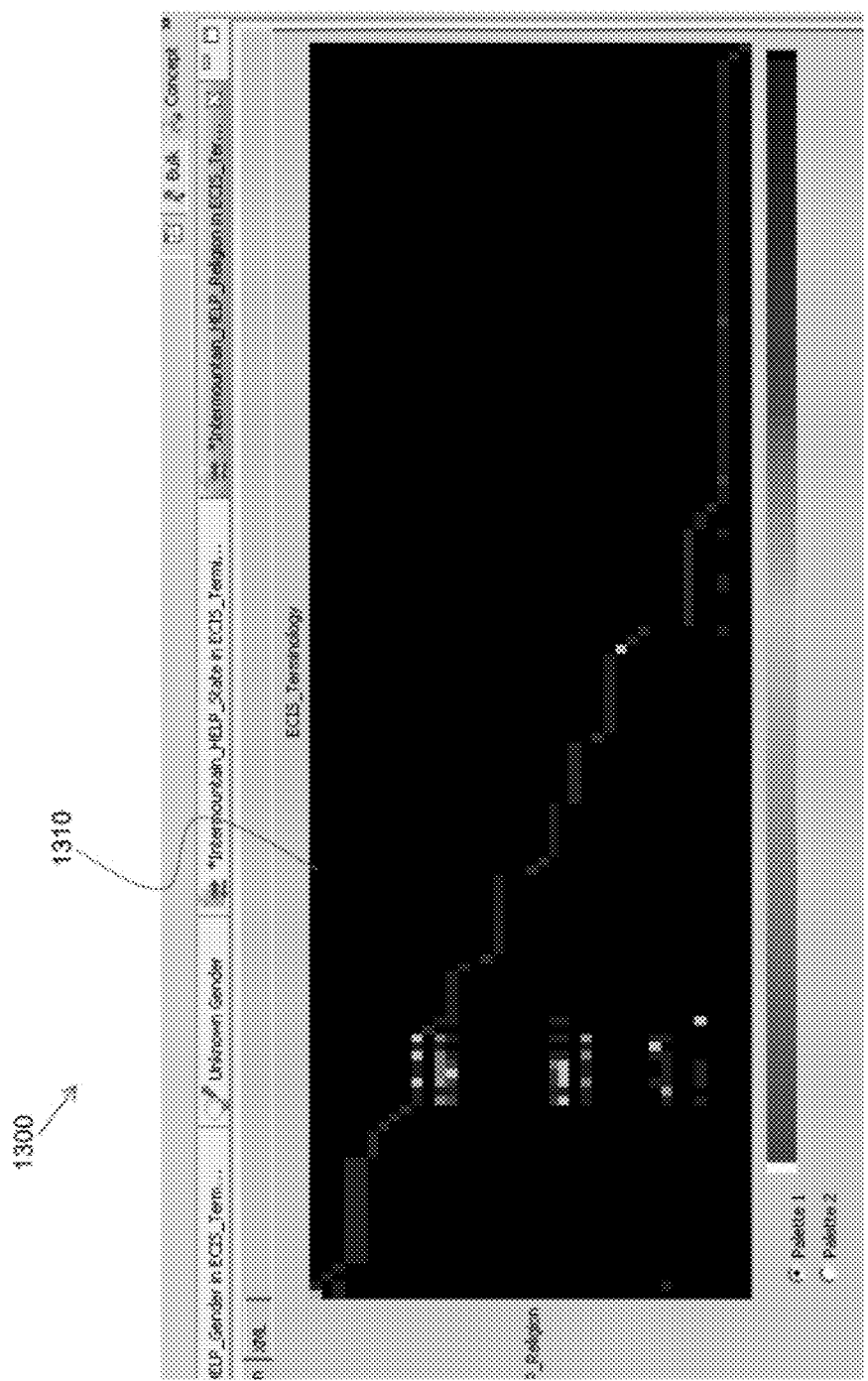
FIG. 13 depicts an example interface showing a closer view of clustering around a particular term.

FIG. 13 depicts an example interface 1300 showing a closer view 1310 of clustering around a particular term. Clusters are displayed according to a selected palette 1320 in the example of FIG. 13. In a heat map example, a "cool" (e.g., blue) color representation indicates a lack of clustering, and a "hot" color (e.g., red) indicates significant clustering and potential for confusion. As shown in the example of FIG. 13, clustering can be exhibited in a range from cool to hot and depicted in the visualization view 1310 for user review. In certain examples, a user can select a point on the visualization to pull up further detail (e.g., a matrix or table view, an editor, etc.).

Figure 15:
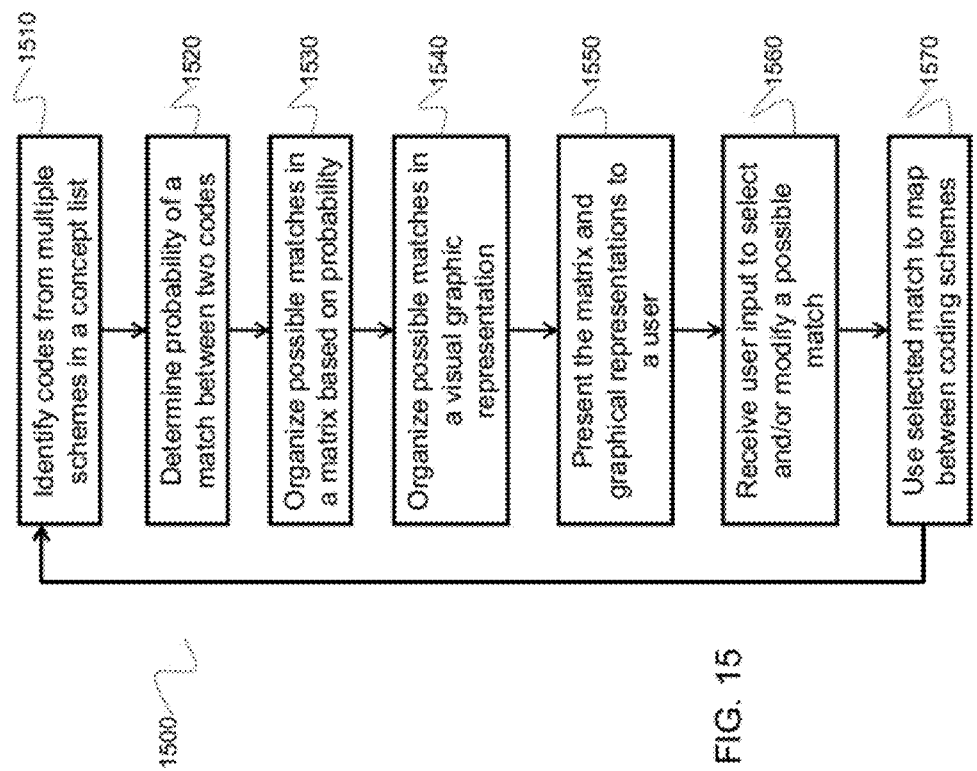
FIG. 15 illustrates a flow diagram for an example method for computer-assisted code scheme to code scheme mapping.

FIG. 15 is a flow diagram representative of example machine readable instructions that can be executed to implement the example systems 400, 500, 1000, 1100, 1200, and/or 1300 of FIGS. 4, 5, 10, 11, 12, and 13 and/or portions of one or more of those systems. The example processes of FIG. 15 can be performed using a processor, a controller and/or any other suitable processing device. For example, the example processes of FIG. 15 can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIG. 15 can be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIG. 15 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIG. 15 can be implemented manually or as any combination(s) of any of the foregoing techniques, for example, any combination of firmware, software, discrete logic and/or hardware. Further, although the example processes of FIG. 15 are described with reference to the flow diagrams of FIG. 15, other methods of implementing the processes of FIG. 15 can be employed. For example, the order of execution of the blocks can be changed, and/or some of the blocks described can be changed, eliminated, sub-divided, or combined. Additionally, any or all of the example processes of FIG. 15 can be performed sequentially and/or in parallel by, for example, separate processing threads, processors, devices, discrete logic, circuits, etc.

FIG. 15 illustrates a flow diagram for an example method 1500 for computer-assisted code scheme to code scheme mapping. At block 1510, codes from two or more code schemes are identified in a concept list. For example, coded concepts from a GE Healthcare code scheme and an Intermountain Healthcare code scheme are identified in a concept list.

At block 1520, a probability that two codes from the list are a match between first and second code schemes is determined. For example, an array of scores is generated wherein each participating code scheme is represented by a dimension and each code in that scheme is a point in that scheme's dimension.

At block 1530, possible matches are organized based on probability in a matrix. For example, if there are two different code schemes, then each code in scheme one represents a row and each code in scheme two represents a column A probability that code three in scheme one is the same as code four in scheme two is the cell value at row three, column four. By creating an M×N matrix (where M is a number of codes in scheme one and N is a number of codes in scheme two), a number of visual and mathematical tools can extract meaning.

At block 1540, possible matches are organized in a visual graphic representation. For example, a graphical representation of concept codes can reveal an existence of macro-scale concept clustering and visually distinguish chaotic "tangles" from coherent "one-to-one" mappings for a user.

At block 1550, the graphic representation and the matrix are presented to a user for review. For example, the visual representation and alphanumeric matrix data can be presented to a user within a single interface, within separate interfaces, etc. A user can select to view the graphical representation and the matrix together and/or separately, for example.

At block 1560, user input is received to select and/or modify a possible match. For example, a user can select a match from the matrix and/or visual (e.g., heat map) representation of coded concepts to confirm a match between the two code schemes. Alternatively or in addition, a user can select a probable match and modify the match to indicate a match of different concepts, a different probability, etc.

At block 1570, the selected match is used to map a concept from the first code scheme to the second code scheme. For example, a selected match is confirmed to map terminology between the code schemes and allow communication between systems utilizing the first and/or second code schemes.

Figure 16:
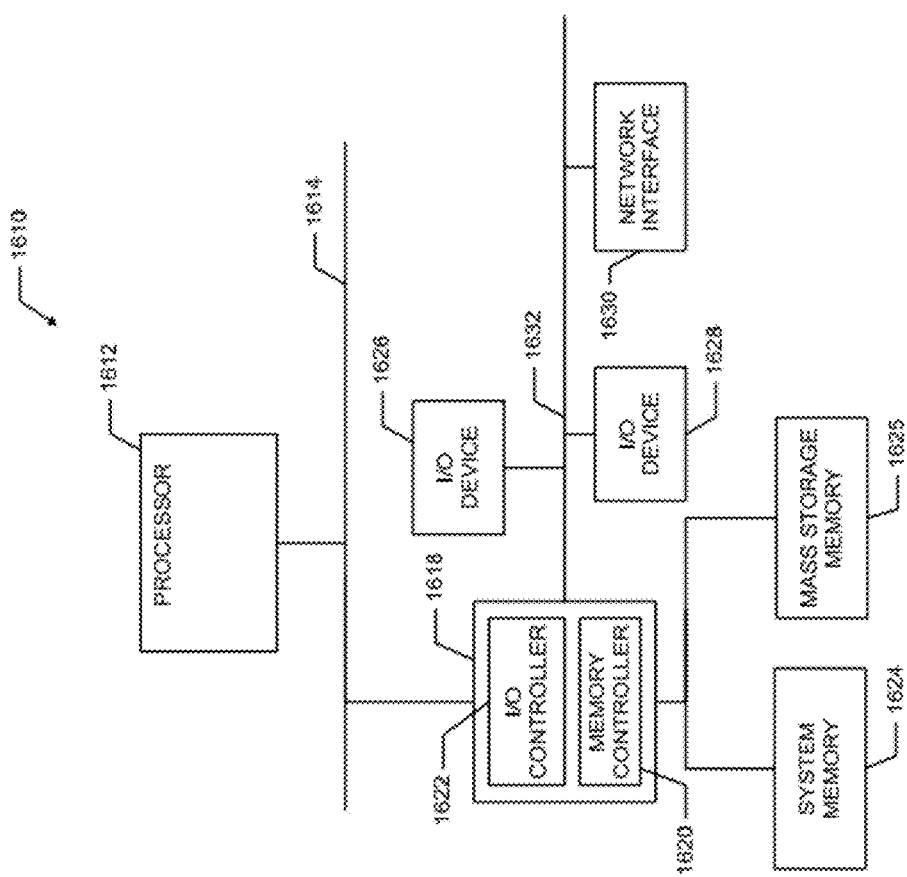
FIG. 16 is a block diagram of an example processor system that may be used to implement systems, apparatus, and methods described herein.

FIG. 16 is a block diagram of an example processor system 1610 that can be used to implement systems, apparatus, and methods described herein. As shown in FIG. 16, the processor system 1610 includes a processor 1612 that is coupled to an interconnection bus 1614. The processor 1612 can be any suitable processor, processing unit, or microprocessor, for example. Although not shown in FIG. 16, the system 1610 can be a multi-processor system and, thus, can include one or more additional processors that are identical or similar to the processor 1612 and that are communicatively coupled to the interconnection bus 1614. For example, "cloud" and/or "grid" based computing can be employed for three dimensional processing using Euclidian vectors and linear algebra, as described above. In certain examples, a Bayesian algorithm can be used in an evolving model combining multiple executions of multiple algorithms. As certain mappings are resolved, a probability associated with other remaining mappings changes.

The processor 1612 of FIG. 16 is coupled to a chipset 1618, which includes a memory controller 1620 and an input/output ("I/O") controller 1622. As is well known, a chipset typically provides I/O and memory management functions as well as a plurality of general purpose and/or special purpose registers, timers, etc. that are accessible or used by one or more processors coupled to the chipset 1618. The memory controller 1620 performs functions that enable the processor 1612 (or processors if there are multiple processors) to access a system memory 1624 and a mass storage memory 1625.

The system memory 1624 can include any desired type of volatile and/or non-volatile memory such as, for example, static random access memory (SRAM), dynamic random access memory (DRAM), flash memory, read-only memory (ROM), etc. The mass storage memory 1625 can include any desired type of mass storage device including hard disk drives, optical drives, tape storage devices, etc.

The I/O controller 1622 performs functions that enable the processor 1612 to communicate with peripheral input/output ("I/O") devices 1626 and 1628 and a network interface 1630 via an I/O bus 1632. The I/O devices 1626 and 1628 can be any desired type of I/O device such as, for example, a keyboard, a video display or monitor, a mouse, etc. The network interface 1630 can be, for example, an Ethernet device, an asynchronous transfer mode ("ATM") device, an 802.11 device, a DSL modem, a cable modem, a cellular modem, etc., that enables the processor system 1610 to communicate with another processor system.

While the memory controller 1620 and the I/O controller 1622 are depicted in FIG. 16 as separate blocks within the chipset 1618, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine accessible or readable medium and executable by, for example, a processor system (e.g., the example processor system 1610 of FIG. 16). When any of the appended claims are read to cover a purely software and/or firmware implementation, at least one of the components is hereby expressly defined to include a tangible medium such as a memory, DVD, CD, Blu-ray disc, etc. storing the software and/or firmware.

Thus, certain examples described herein facilitate use of reduced manpower associated with manually matching terms between two or more code schemes, as well as helping to provide faster interoperability configuration. Certain examples provide more reliable concept matching by computer-generated determination of match probabilities augmented by user confirmation. Certain examples provide both alphanumeric and graphical representations of likely concept matches for both automated and manual review and confirmation of a probable concept match. Certain examples provide technical effects of advanced analytics, real-time decision support, and business intelligence through use of structured, coded data. Certain examples help reduce costs incurred due to redundant and disparate data definition, storage, and maintenance and help promote national and international interoperability by sharing terminology with the healthcare community at large.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media can be any available media that can be accessed by a general purpose or special purpose computer or other machine with a processor. By way of example, such computer-readable media can include RAM, ROM, PROM, EPROM, EEPROM, Flash, CD-ROM, DVD, Blu-ray or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions include, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention can be practiced in a networked environment using logical connections to one or more remote computers having processors. Logical connections can include a local area network (LAN) and a wide area network (WAN) that are presented here by way of example and not limitation. Such networking environments are commonplace in office-wide or enterprise-wide computer networks, intranets and the Internet and can use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention can also be practiced in distributed computing environments where tasks are performed by local and remote processing devices that are linked (either by hardwired links, wireless links, or by a combination of hardwired or wireless links) through a communications network. In a distributed computing environment, program modules can be located in both local and remote memory storage devices.

While the invention has been described with reference to certain embodiments, it will be understood by those skilled in the art that various changes can be made and equivalents can be substituted without departing from the scope of the invention. In addition, many modifications can be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for mapping of medical code schemes, said method comprising:
   processing a plurality of coded concepts to determine a potential match between a code from a first code scheme in the plurality of coded concepts and a code from a second code scheme in the plurality of coded concepts;
   assigning a probability to each potential match of a code from the first code scheme and a code from the second code scheme;
   generating an alphanumeric indication of the probability of each potential match between the first code scheme and the second code scheme from the plurality of coded concepts;
   generating a graphical representation of the plurality of coded concepts; outputting the alphanumeric indication and the graphical representation to a user; and accepting user input to select a match between the first code scheme and the second code scheme;
   wherein, for the first code scheme and the second code scheme, each code in the first scheme represents a row and each code in the second code scheme represent a column in the matrix such that the probability that a code in the first code scheme is the same as a code in the second code scheme is represented by a cell value at a corresponding matrix position row and column position;
   wherein the graphical representation comprises a heat map highlighting tight correlation and clustering of coded concepts in relation to probability of each potential match;
   wherein the heat map and the alphanumeric indication facilitate bulk matching of coded concepts among a plurality of code schemes based at least in part on concept clustering and visual distinction between clusters of concepts and one-to-one mappings.

2. The method of claim 1, wherein the alphanumeric indication comprises a matrix of potential matches between codes from the first code scheme and codes from the second code scheme.

3. The method of claim 2, wherein the graphical representation is rendered using probability match data found in the matrix.

4. The method of claim 1, further comprising mapping between the first code scheme and the second code scheme using the user selected match to facilitate interoperability between a first system utilizing the first code scheme and a second system utilizing the second code scheme.

5. A system for mapping of medical code schemes, said system comprising a processor to implement:
   a code analyzer to process a plurality of coded concepts to determine a potential match between a code from a first code scheme in the plurality of coded concepts and a code from a second code scheme in the plurality of coded concepts and to assign a probability to each potential match of a code from the first code scheme and a code from the second code scheme, the code analyzer to generate an alphanumeric indication of the probability of each potential match between the first code scheme and the second code scheme from the plurality of coded concepts and to generate a graphical representation of the plurality of coded concepts; and a user interface to output the alphanumeric and the graphical representation to a user and to accept user input to select a match between the first code scheme and the second code scheme;

wherein, for the first code scheme and the second code scheme, each code in the first scheme represents a row and each code in the second code scheme represent a column in the matrix such that the probability that a code in the first code scheme is the same as a code in the second code scheme is represented by a cell value at a corresponding matrix position row and column position;

wherein the graphical representation comprises a heat map highlighting tight correlation and clustering of coded concepts in relation to probability of each potential match;

wherein the heat map and the alphanumeric indication facilitate bulk matching of coded concepts among a plurality of code schemes based at least in part on concept clustering and visual distinction between clusters of concepts and one-to-one mappings.

6. The system of claim 5, wherein the alphanumeric indication comprises a matrix of potential matches between codes from the first code scheme and codes from the second code scheme.

7. The system of claim 6, wherein the graphical representation is rendered using probability match data found in the matrix.

8. The computer readable storage medium of claim 6, wherein the graphical representation is rendered using probability match data found in the matrix.

9. The system of claim 5, further comprising mapping between the first code scheme and the second code scheme using the user selected match to facilitate interoperability between a first system utilizing the first code scheme and a second system utilizing the second code scheme.

10. The computer readable storage medium of claim 5, wherein the alphanumeric indication comprises a matrix of potential matches between codes from the first code scheme and codes from the second code scheme.

11. A tangible computer readable storage medium including executable program instructions which, when executed by a computer processor, cause the computer to implement a medical code scheme bulk matching system, said system comprising:

a code analyzer to process a plurality of coded concepts to determine a potential match between a code from a first code scheme in the plurality of coded concepts and a code from a second code scheme in the plurality of coded concepts and to assign a probability to each potential match of a code from the first code scheme and a code from the second code scheme, the code analyzer to generate an alphanumeric indication of the probability of each potential match between the first code scheme and the second code scheme from the plurality of coded concepts and to generate a graphical representation of the plurality of coded concepts; and a user interface to output the alphanumeric and the graphical representation to a user and to accept user input to select a match between the first code scheme and the second code scheme;

wherein, for the first code scheme and the second code scheme, each code in the first scheme represents a row and each code in the second code scheme represent a column in the matrix such that the probability that a code in the first code scheme is the same as a code in the second code scheme is represented by a cell value at a corresponding matrix position row and column position;

wherein the graphical representation comprises a heat map highlighting tight correlation and clustering of coded concepts in relation to probability of each potential match;

wherein the heat map and the alphanumeric indication facilitate bulk matching of coded concepts among a plurality of code schemes based at least in part on concept clustering and visual distinction between clusters of concepts and one-to-one mappings.

* * * * *